United States Patent [19]

Sadowski et al.

[11] Patent Number: 5,885,779
[45] Date of Patent: Mar. 23, 1999

[54] REPRESSED TRANS-ACTIVATOR SYSTEM FOR CHARACTERIZATION OF PROTEIN-PROTEIN INTERACTIONS

[75] Inventors: Ivan Sadowski, Delta; Martin Hirst, Tsawwassen; John Rohde, Vancouver, all of Canada

[73] Assignee: University of British Columbia, Vancouver, Canada

[21] Appl. No.: 926,623

[22] Filed: Sep. 9, 1997

[51] Int. Cl.$^6$ .............................. C12Q 1/68; C12N 15/63; C12N 5/10; C12N 15/11

[52] U.S. Cl. ....................... 435/6; 435/69.7; 435/91.41; 435/320.1; 435/325; 435/254.2; 530/350; 536/23.4; 536/23.5; 536/23.7; 536/24.33

[58] Field of Search ........................ 435/6, 69.7, 320.1, 435/325, 410, 243, 254.2; 536/23.4, 24.33; 530/350

[56] References Cited

U.S. PATENT DOCUMENTS

| | | | |
|---|---|---|---|
| 5,283,173 | 2/1994 | Fields et al. | 435/6 |
| 5,468,614 | 11/1995 | Fields et al. | 435/6 |
| 5,525,490 | 6/1996 | Erickson et al. | 435/29 |
| 5,580,736 | 12/1996 | Brent et al. | 435/69.1 |

OTHER PUBLICATIONS

Fields et al. the two–hybrid system: an assay for protein-–protein interactions. Trends in Genetics vol. 10 pp. 286–292, 1994.

Tzamarias, Dimitris et al., "Functional Dissection of the Yeast Cyc8–Tup1 Transcriptional Co–Repressor Complex," *Nature* (1994), vol. 369, (30):758–761.

Sadowski, Ivan "Uses For Gal4 Expression In Mammalian Cells," *Genetic Engineering* (1995) vol. 17:119–148.

"Matchmaker LexA Two–Hybrid System," *CLONTECHniques* (Jul. 1996) vol. 11:14–17.

EMBO Course: Yeast Two Hybrid/Interaction Trap System (online) EMBO 1996 [retrieved on or before Sep. 5, 1997]. Information Sheet. [retrieved from the internet, <URL:http://www.embo.org.html>.

"HybriZAP Two–Hybrid Vector Kits," *Two–Hybrid Vector p. 34, Stratagene Catalog p. 34*.

Invitrogen Catalogue (online). Invitrogen 1997. [retrieved on or before Sep. 5, 1997]. Datasheet for Hybrid Hunter: Improved Two Hybrid System for the Detection of Protein-–Protein Interactions [retrieved from the Internet:<URL:http://www.invitrogen.com/catalogue-.html>.

Sadowski, Ivan et al., "GAL4 Fusion Vectors For Expression In Yeast Or Mammalian Cells," *Gene* (1992) vol. 118:137–141.

*Primary Examiner*—George C. Elliott
*Assistant Examiner*—John S. Brusca
*Attorney, Agent, or Firm*—Bozicevic & Reed LLP; Bret E. Field

[57] ABSTRACT

The invention provides a system for assaying protein-protein interactions. Amino acid sequences of interest are inserted into 'bait' and 'prey' fusion proteins. The bait fusion proteins include a DNA-binding domain. The prey fusion proteins include a transcriptional repression domain. The interaction of the bait and prey fusion proteins is detected by the repression of reporter genes. The reporter genes have operator sequences to which the DNA-binding domain of the bait fusion protein can bind. The reporter genes are expressed unless the prey fusion protein interacts with a bait fusion protein at the operator region of the reporter gene. When a prey fusion protein binds to a bait fusion protein, the expression of the reporter gene is repressed. Compounds that interfere with the interaction of bait and prey fusion proteins may be detected by their ability to reverse the repression of the reporter genes.

27 Claims, 12 Drawing Sheets

A) No Glucose (+ galactose)

B) Glucose (+ galactose)

A) TUP1 protein

B) TUP1 repression domain fused to LexA DBD

A) Endogenous *GAL1* gene.

B) *GAL1-URA3* integrated at *ADE2*.

C) *GAL1-LacZ* integrated at *MFA2*.

D) *GAL1-CAN1* integrated at *LYS2*.

A

B

REPRESSED TRANS-ACTIVATOR SYSTEM FOR CHARACTERIZATION OF PROTEIN-PROTEIN INTERACTIONS

BACKGROUND OF THE INVENTION

Virtually all cellular responses, including growth and differentiation, are stringently controlled by physiological signals in the form of growth factors, hormones, nutrients, and contact with neighbouring cells. These various signals are processed and interpreted by signal transduction mechanisms which ultimately induce the cell to mount an appropriate response. Signalling pathways stimulated by physiological signals involves a network of specific protein-protein interactions which function to transmit the signal to downstream effector molecules that execute the response (32). Thus specific interactions between proteins are critical for signal transduction mechanisms as well as regulation of cellular architecture and responses to physiological signals. Given that specific protein-protein interactions are involved in execution of virtually all cellular functions, technologies which simplify and facilitate detection and analysis of specific protein-protein interactions will be valuable for the discovery, design and testing of drugs that target highly specific biological processes.

Transcriptional Activators and Regulation of Eukaryotic Transcription

Eukaryotic gene expression is regulated by a class of proteins known as transcriptional activators, or enhancer binding proteins. These molecules, bind to specific sequences on DNA within the promoters of genes they regulate, and function by recruiting the general transcriptional initiation complex to the site where transcription of DNA into messenger RNA begins (33). Recent experiments suggest that the general eukaryotic transcriptional initiation complex consists of two large protein complexes represented by transcription factor IID (TFIID), which contains the TATA-element binding protein that functions to position the general initiation complex at a precise location on the promoter, and the RNA polymerase II holoenzyme, which contains the catalytic function necessary to unwind the double stranded DNA and transcribe a copy of the DNA template into messenger RNA (42). Known transcriptional activators are understood to function by forming direct protein-protein interactions with parts of TFIID and/or the RNA polymerase holoenzyme, and catalysing their assembly into an initiation complex at the TATA-element of the promoter.

Regulation of the GAL Genes in Saccharomyces, a Paradigm for Eukaryotic Transcriptional Regulation Proteins that regulate the expression of eukaryotic genes typically possess two functional elements, a site-specific DNA-binding domain and a transcriptional activation domain which can interact with either TFIID or the RNA polymerase holoenzyme. Eukaryotic transcriptional regulatory proteins are typified by the Saccharomyces yeast GAL4 protein, which was one of the first eukaryotic transcriptional activators on which these functional elements were characterized (33, 35). GAL4 is responsible for regulation of genes which are necessary for utilization of the six carbon sugar galactose. Galactose must be converted into glucose prior to catabolism; in Saccharomyces this process typically involves four reactions which are catalysed by five different enzymes. Each enzyme is encoded by a GAL gene (GAL 1, 2, 5, 7, and 10) which is regulated by the transactivator GAL4 in response to the presence of galactose. Each GAL gene has a cis-element within the promoter, termed the upstream activating sequence for galactose ($UAS_G$), which contains 17 base-pair sequences to which GAL4 specifically binds. The GAL genes are repressed when galactose is absent, but are strongly and rapidly induced by the presence of galactose. GAL4 is prevented from activating transcription when galactose is absent by a regulatory protein GAL80. GAL80 binds directly to GAL4 and likely functions by preventing interaction between GAL4's activation domains and the general transcriptional initiation factors. When yeast are given galactose, transcription of the GAL genes is induced. Galactose causes a change in the interaction between GAL4 and GAL80 such that GAL4's activation domains become exposed to allow contact with the general transcription factors represented by TFIID and the RNA polymerase II holoenzyme and catalyse their assembly at the TATA-element which results in transcription of the GAL genes.

The GAL4 Protein

The functional regions of GAL4 have been carefully defined by a combination of biochemical and molecular genetic strategies (35). GAL4 binds as a dimer to its specific cis-element within the $UAS_G$ of the GAL genes. The ability to form tight dimers and bind specifically to DNA is conferred by an N-terminal DNA-binding domain. This fragment of GAL4 (amino acids 1–147) can bind efficiently and specifically to DNA but cannot activate transcription. Two parts of the GAL4 protein are necessary for activation of transcription, called activating region 1 and activating region 2. The activating regions are thought to function by interacting with the general transcription factors. The large central portion of GAL4 between the two activating regions is required for inhibition of GAL4 in response to the presence of glucose. The C-terminal 30 amino acids of GAL4 bind the negative regulatory protein GAL80; deletion of this segment causes constitutive induction of GAL transcription.

The Interaction Trap and Standard Two-Hybrid Assay

The yeast two-hybrid and interaction trap systems provide powerful approaches towards characterizing protein-protein interactions in vivo. Both strategies exploit the fact that the transcriptional activation and DNA binding domains of most eukaryotic transcriptional activators function when expressed as fusions with heterologous proteins (7), and can transactivate when brought together by specific protein-protein interaction between separate fusions (10, 14). An important contribution towards development of these systems was the discovery that some transcriptional activator proteins, notably the Herpes viral protein 16 (VP16), are indirectly recruited to DNA through interaction with a sequence specific DNA binding protein (46). VP16 activates transcription by forming a complex with the cellular proteins Oct-1 and HCF; the Oct-1/HCF/VP16 complex binds to enhancer elements of the Herpes immediate early genes (43). It was subsequently shown that the negative regulatory protein GAL80 could be converted into a GAL4-dependent transactivator by fusion of a short negatively-charged transcriptional activating sequence B17 (30). The GAL80-B17 fusion protein, when co-expressed with GAL4, was found to cause activation of a GAL4-dependent reporter gene to a greater extent than GAL4 alone (30). A similar experiment performed more recently, was used to examine interaction between GAL4 and GAL80 in vivo following induction (28).

The initial "two-hybrid" experiment showed that specific protein-protein interaction between Snf1p and Snf4p, neither of which are transactivators themselves, could bring the DNA-binding and C-terminal transactivation domains of GAL4 together to form a functional transactivator when expressed as separate fusions (14). In the standard two-hybrid system a protein of interest is fused to the DNA-binding domain of GAL4 to create a "bait" fusion protein. Proteins that interact with the bait protein, termed the "prey" can be identified by their ability to cause transactivation of a GAL4-dependent reporter gene when expressed as a fusion to the C-terminal transactivation domain of GAL4 (10, 15, 16). The "interaction trap" system employs the identical principle of using separate fusions with DNA-binding and transactivation domains, except that the bait is fused to LexA, which is a sequence-specific DNA binding protein from *E. coli*, and an artificial transactivation domain known as B42 (31) is used for the "prey" fusions. Interaction between the bait and prey fusions is detected by expression of a LexA-responsive reporter gene (6).

Transcriptional Activator Proteins Cannot be Used for Standard Two-Hybrid Analysis One major limitation of the standard two-hybrid and interaction trap systems is that bait proteins which are themselves capable of activating transcription cannot be used as bait because they cause activation of the reporter genes on their own without interacting with a prey-activating domain fusion protein. This is unfortunate because transcriptional regulatory proteins represent key molecules controlling most cellular processes; most transcriptional regulatory proteins naturally activate transcription when fused to a heterologous DNA-binding domain. The yeast genome sequence has indicated that a surprisingly large fraction of even a simple eukaryote is predicted to encode transcriptional regulatory proteins (17). The life cycle of the yeast Saccharomyces involves only four distinct differentiated states. By comparison, human development must involve a significantly greater number of transcriptional regulators to coordinate differentiation of thousands of different cell types. For this reason alone it is critical that simple and reliable strategies become available which allow characterization of protein-protein interactions made by eukaryotic transactivators.

The requirement that the bait fusion must be incapable of activating transcription for use in the two-hybrid and interaction trap systems is a limitation that also applies to many proteins whose function does not normally involve transcriptional regulation. Approximately 10 to 15% of proteins that do not normally function as transcription factors may artificially cause activation of transcription when fused to a DNA-binding domain (31, 34). This is illustrated by experiments which showed that at least 10% of random protein fragments fused to the GAL4-DNA binding domain caused activation of transcription in yeast (31, 34). These results suggest that many amino acid sequences that interact with the large RNA polymerase holoenzyme complex may cause transcriptional activation when fused to a DNA-binding domain (3).

It is possible to use the two-hybrid assay to identify compounds that interfere with particular protein-protein interactions. In the two-hybrid assay, such interference will result in a negative signal, i.e. failure to obtain expression of the reporter gene. There are, however, problems associated with relying on a negative signal, i.e. lack of expression, to identify such compounds. Failure to obtain expression may be caused by factors other than interference with the protein-protein interaction of interest. For example, compounds that interfere with transcription may score a false positive result. Similarly, compounds that generally inhibit cell growth may score a false positive result by appearing to interfere with the expression of a reporter gene that would confer survival on a restrictive medium.

Reverse Two-Hybrid Assay

A modification of the standard two-hybrid system known as "Reverse Two-Hybrid" (27; Erickson et al. U.S. Pat. No. 5,525,490, Vidal et al. International Application Number PCT/US96/04995) has been described which is intended for use in identifying specific inhibitors of a standard two-hybrid protein-protein interaction. The reverse two-hybrid system operates by driving the expression of relay gene, such as the GAL80 gene, that encodes a protein that binds to and masks the activation domain of a transcriptional activator such as GAL4. Expression of the reporter genes is made dependant upon the functioning of the activation domain of the transcriptional activator. Only when the level of the masking protein is reduced because a compound interferes with the two-hybrid interaction will the activation domain of the transcriptional activator be unmasked and allowed to function.

There are however, problems associated with the use of the reverse two-hybrid assay to identify compounds that interfere with selected protein-protein interactions. For example, compounds that interfere with the interaction between the masking protein and the transcriptional activator will score false positive results. False positives will also arise where the "bait" fusion protein acts as a transcriptional activator because the masking protein will not mask such activity. As indicated above, this latter problem is exacerbated by the fact that many proteins and protein fragments appear to function as transcriptional activators when fused to a DNA-binding domain.

Transcriptional Repression

While most genes are controlled in a positive manner by transcriptional activators, there are also mechanisms for repressing or inhibiting transcription in response to physiological signals. Several proteins have been identified which function as general repressors of transcription. Some of the first eukaryotic transcriptional repressors described include the yeast protein encoded by TUP1, and the *Drosophila Kruppel* protein, although there are now many different proteins which have been demonstrated to cause transcriptional repression (19).

Specific amino acid sequences within transcriptional repressor proteins have been identified that are capable of causing repression of transcription when fused to a heterologous DNA-binding domain (19, 35). Such transcriptional repressor domains have been identified in many eukaryotic transcriptional repressers. Transcriptional repressor domains need not be structurally similar, they are defined by their common ability to repress transcription.

TUP1 is a 713 amino acid long protein which is required for inhibiting transcription of specific classes of genes in response to physiological signals and the differentiation state of the yeast cell. The current understanding is that TUP1 does not bind directly to DNA, but rather interacts with specific DNA-binding proteins bound at cis-elements known as upstream repression sequences (URS) in a complex with the product of SSN6 (50, 45, 12). TUP1 has been demonstrated to be responsible for active repression in an experiment in which TUP1 fragments were fused directly to the *E.* coli DNA-binding protein LexA (47). LexA-TUP1 fusions were found to inhibit transcription of a reporter gene which contained upstream binding sites for LexA (47). In this system, only the N-terminal 200 residues of TUP1 were necessary to mediate repression. This experiment was similar to previous experiments which demonstrated transcriptional repressor domains in other eukaryotic transcriptional repressors (19, 35). The holoenzyme-associated cyclin-dependent protein kinase SRB10 is required for repression of transcription by TUP1(48).

SUMMARY OF THE INVENTION

The system of this invention, termed the repressed transactivator (RTA) system, detects protein-protein interactions by repression of reporter genes. In the RTA system, interaction between a 'bait' fusion protein having a DNA-binding domain, such as the DNA-binding domain of GAL4 or LexA (FIG. 2, Protein X), with a 'prey' fusion protein having a repression domain, such as the N-terminal TUP1 repression domain (FIG. 2, Protein Y-RD) causes inhibition of expression, i.e. repression, of specific reporter genes.

The 'bait' fusion protein may be a transcriptional activator protein (which is not possible with the two-hybrid and interaction trap systems of the prior art). Alternatively, the reporter genes and/or bait fusion proteins may be modified to themselves include transcriptional activator activity, which allows the assay of this invention to be performed on bait fusion proteins that do not activate transcription.

The 'prey' fusion protein causes repression of reporter genes that would other wise be active, such as the GAL4-dependent reporter genes GAL1-CAN1, GAL1-URA3, the endogenous GAL1 gene, and a GAL1-LacZ fusion gene. Using these reporter genes, inhibition of GAL4-dependent reporter gene expression may be indicated by growth on canavanine, 5-FOA, and 2-deoxygalactose, and formation of blue colonies on X-gal, respectively.

The RTA system of the invention can also be employed for use in identifying and characterizing specific compounds that inhibit protein-protein interactions. In the RTA system, inhibitors of a specific protein-protein interaction will interfere with recruitment of the repressor function of the prey fusion protein, resulting in activation of reporter gene expression. The fact that such an assay is based on activation of reporter gene expression, rather than lack of activation in the standard two-hybrid assay, may make the RTA system preferable to the two-hybrid system for screening for a inhibitors of protein-protein interactions.

This invention provides cells for assaying interactions between fusion proteins, the cells comprising a first recombinant gene, a second recombinant gene and a recombinant reporter gene. The cells may, for example, be *Saccharomyces cerevisiae* cells, *Schizosaccharomiyces pombe* cells, or mammalian tissue culture cells. The first recombinant gene codes for a prey fusion protein. The first recombinant gene may be under the control of a repressable promoter, such as a promoter homologous to the MET3 promoter. The prey fusion protein comprises a transcriptional repressor domain and a first heterologous amino acid sequence. The second recombinant gene codes for a bait fusion protein, the bait fusion protein comprising a DNA-binding domain and a second heterologous amino acid sequence. The DNA-binding domain may include sequences homologous to the DNA-binding domain of GAL4 or LexA. The recombinant reporter gene codes for a detectable gene product. The recombinant reporter gene comprises an operator DNA sequence within its promoter capable of binding the DNA-binding domain of the bait fusion protein. The reporter gene is expressed in the absence of binding between the prey fusion protein and the bait fusion protein, such absence of binding being the result of an absence of binding between the first heterologous amino acid sequence and the second heterologous amino acid sequence. The reporter gene is repressed when there is binding between the first heterologous amino acid sequence and the second heterologous amino acid sequence. The promoter of the reporter gene may include a binding site for additional transactivator proteins, such as GCN4.

The bait fusion protein may include a transcriptional activator domain, such as sequences homologous to amino acids 147–238 (activating region 1) of GAL4.

The transcriptional repressor domain may include sequences homologous to the transcriptional repressor domain of the yeast TUP1 protein, the transcriptional repressor domain of the *Drosophila Kruppel* protein, the transcriptional repressor domain of the *Drosophila engrailed* protein, the transcriptional repressor domain of the *Drosophila knirps* protein, the transcriptional repressor domain of the Drosophila even-skipped protein, the transcriptional repressor domain of the Drosophila paired protein, the transcriptional repressor domain of the mammalian Egr-1 protein, the transcriptional repressor domain of the mammalian WT1 protein, the transcriptional repressor domain of the mammalian RARa protein, or the transcriptional repressor domain of the mammalian KRAB protein.

In yeast cells, the reporter gene may be homologous the yeast URA3 gene, the yeast CAN1 gene, the yeast GAL1 gene, the yeast HIS3 gene, or the *E. coli* LacZ gene. In mammalian cells, the reporter gene may be homologous to the CAT gene, the LacZ gene, the SEAP gene, the Luciferase gene, the GFP gene, the BFP gene, the CD2 gene, the Flu HA gene, or the tPA gene.

This invention provides a kit for making cells for assaying interactions between fusion proteins. The kit includes a first vector for expressing a prey fusion protein with a transcriptional repressor domain, a second vector for expressing a bait fusion protein with a DNA-binding domain, and host cells having a recombinant reporter gene coding for a detectable gene product. The first vector includes an expressible gene having an insertion site and a sequence coding for the transcriptional repressor domain. The second vector has an expressible gene having an insertion site and a sequence coding for the DNA-binding domain. The recombinant reporter gene in the host cells has an operator DNA sequence capable of binding to the DNA-binding domain of the bait fusion protein. The reporter gene is expressed in the absence of binding between the prey fusion protein and the bait fusion protein, such absence of binding being the result of an absence of binding between the first heterologous amino acid sequence and the second heterologous amino acid sequence. The reporter gene is repressed when there is binding between the first heterologous amino acid sequence and the second heterologous amino acid sequence. The kit may also include oligonucleotide primers homologous to sequences flanking the insertion sites in the first and second vectors.

The cells in the kit may be yeast cells. The transcriptional repressor domain of the prey fusion protein may be homologous to the transcriptional repressor domain of TUP1. The DNA-binding domain of the bait fusion protein may be homologous to the DNA-binding sequence of GAL4. The operator of the reporter gene may have a DNA sequence homologous to the GAL4 protein binding sequence of the GAL1 gene. The reporter gene may be homologous to the CAN1 gene, the URA3 gene or the LacZ gene.

This invention provides a method of assaying for interactions between fusion proteins in cells. The method involves the following steps:

Providing the cells with a recombinant reporter gene coding for a detectable gene product. The recombinant reporter gene includes an operator DNA sequence capable of binding to a DNA-binding domain of a bait fusion protein.

Causing the cells to express a recombinant gene coding for a prey fusion protein which includes a transcriptional repressor domain and a first heterologous amino acid sequence.

Causing the cells to express a recombinant gene coding for the bait fusion protein which includes the DNA-binding domain and a second heterologous amino acid sequence.

The reporter gene is expressed in the absence of binding between the prey fusion protein and the bait fusion protein, such absence of binding being the result of an absence of binding between the first heterologous amino acid sequence and the second heterologous amino acid sequence. The reporter gene is repressed when there is binding between the first heterologous amino acid sequence and the second heterologous amino acid sequence.

Interaction between the bait and prey fusion proteins is detected by assaying for loss of expression of the detectable gene product. In yeast cells, for example, interaction between the bait and prey fusion proteins may be detected by growth of the cells on canavanine when CAN1 is the reporter gene, by growth on 5-FOA when URA3 is the reporter gene, by growth on 2-deoxygalactose when GAL1 is the reporter gene, by absence of growth on medium lacking histidine where the reporter gene is HIS3 or by the formation of blue colonies when the cells are grown on medium containing X-gal.

This invention provides a method of assaying the ability of compounds to interfere in the interaction between fusion proteins in cells. The method involves the following steps:

Providing the cells with a recombinant reporter gene coding for a detectable gene product. The operator DNA sequence of the reporter gene being capable of binding to a DNA-binding domain of a bait fusion protein.

Causing the cells to express a recombinant gene coding for a prey fusion protein with a transcriptional repressor domain and a first heterologous amino acid sequence.

Causing the cells to express a recombinant gene coding for the bait fusion protein with the DNA-binding domain and a second heterologous amino acid sequence. The second heterologous amino acid sequence being capable of binding to the first heterologous amino acid sequence.

The ability of an exogenous compound to interfere with the binding the bait and prey fusion proteins is tested by assaying for expression of the detectable gene product. The reporter gene is expressed in the absence of binding between the bait and prey fusion proteins, which reflects an absence ob binding between the first heterologous amino acid sequence and the second heterologous amino acid sequence. The reporter gene is repressed when there is binding between the first heterologous amino acid sequence and the second heterologous amino acid sequence.

A "DNA-binding domain" is a sequence of amino acids that are capable of binding to a specific DNA sequence.

A "transcriptional repressor domain" is a sequence of amino acids that is capable of inhibiting transcription when appropriately positioned near the transcription start site of a gene.

A "fusion protein" is a protein made up of amino acid sequences derived from at least two different sources. In the context of a fusion protein, a "heterologous" amino acid sequence is a sequence that comes from a different source than other parts of the fusion protein.

An amino acid sequence is "homologous" to another amino acid sequence if the two sequences are at least 80% identical and the functional activity of the sequences is conserved (for example both sequence function as a DNA-binding domain or both sequences function as a transcriptional repressor domain).

A detectable gene product is a nucleotide or amino acid sequence that can be detected by an assay. Preferably, the expression of a detectable gene product confers on a cell a characteristic that allows the cell to be conveniently selected away from other cells that do not express the detectable gene product.

A "repressable promoter" is a DNA sequence that promotes transcription of a gene to which it is operably connected only under certain conditions, and under other conditions the repressable promoter sequence does not promote expression of the gene. In this context, the conditions that vary the function of the repressable promoter are typically physiological conditions, such as the presence or absence of a particular compound in the media in which a cell lives.

A "transactivator protein" is a protein that can bind to the operator region of a gene and thereby promote transcription of the gene.

BRIEF DESCRIPTION OF THE DRAWINGS

FIG. 3A. In the absence of glucose (and the presence of galactose), the GAL genes are activated by GAL4 protein 21 bound to the $UAS_G$ 20. MIG1 protein 22 binds to the upstream repression sequence (URS) 23, but does not affect GAL transcription in the absence of glucose. FIG. 3B. In the presence of glucose, a complex consisting of the TUP1 26 and SSN6 25 proteins is recruited to the MIG1 protein. TUP1 contains a repression domain which inhibits the general transcription factors and causes repression of GAL gene transcription.

FIG. 4A. Schematic representation of the Saccharomyces TUP1 protein. The N-terminal 200 amino acids of TUP1 contain the transcriptional repression domain 31. FIG. 4B. Fusion of the TUP1 repression domain 31 to the E. coli LexA protein 32 produces a chimeric protein which is capable of causing repression of a reporter gene controlled by the transcriptional activator GCN4 34 and which bears upstream LexA operators 33.

FIG. 5A: Endogenous GAL1 gene. FIG. 5B: GAL1-URA3 integrated at the ADE2 locus. FIG. 5C: GAL1-LacZ integrated at MFA2. FIG. 5D: GAL1-CAN1 integrated at the LYS2 locus.

FIG. 6A: Diagram of the pY vectors in which the ADH1 promoter (pADH) is used to express the GAL4 DNA-binding domain (GAL4 DBD). The DBD is followed by a multiple cloning site (MCS) and translational termination codons in each reading frame (not indicated). The plasmids have a yeast autonomous replication sequence and centromere fragment (ARS-CEN) and the TRP1 gene for propagation and selection in yeast, and an ampicillin a resistance gene (Amp) for selection in E. coli. pY1, pY2, and pY3 are identical except that the multiple cloning site is staggered by a single nucleotide relative to each other to simplify construction of in-frame fusions (36). GAL4-bait transcripts are terminated within the ADH1 terminator (tADH). FIG. 6B: Diagram of the pG vectors which are identical to the pY plasmids except that the GAL4 DNA-binding domain is expressed from the GAL4 promoter (pGAL4).

FIG. 10A: A eukaryotic cell is constructed which expresses GAL4-bait and TUP1-prey fusions whose interaction inhibits expression of a reporter gene. FIG. 10B: Addition of an inhibitor of the bait and prey interaction 41 causes induction of the reporter gene, whose product can be detected biochemically or genetically.

DETAILED DESCRIPTION OF THE INVENTION

Figure 1:
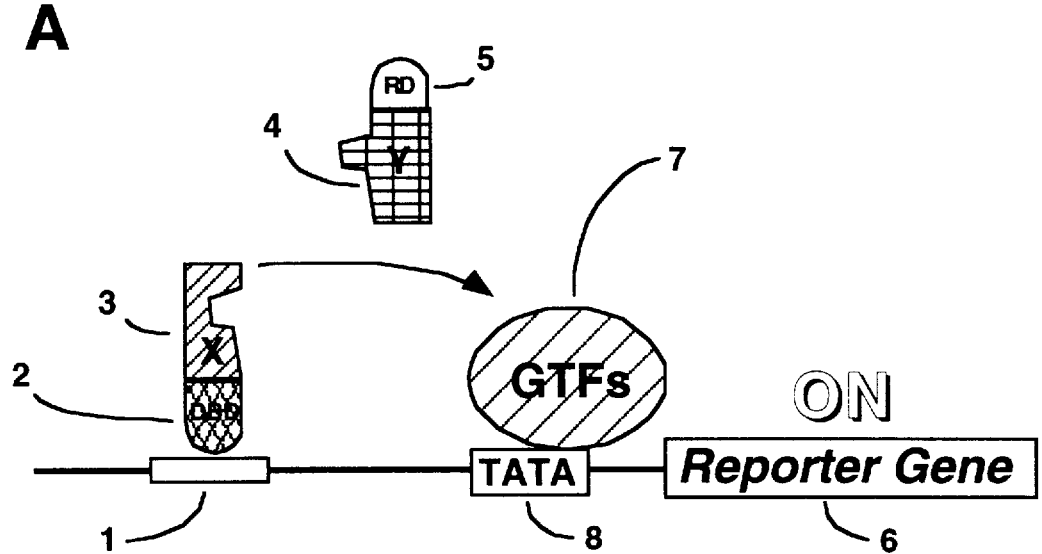
FIG. 1: Schematic representation of the repressed transactivator system (RTA). Panel A. A bait fusion protein consisting of a transcriptional activator protein 3 fused to a site-specific DNA binding domain 2 causes activation of reporter gene 6 expression by binding to its cognate cis-element 1 within the promoter and recruiting the general transcription factors 7 (GTFs) to the TATA element 8. Panel B. Interaction between the transactivator bait fusion and a prey protein fused to a transcriptional repression domain causes inhibition of reporter gene expression.
Figure 1:
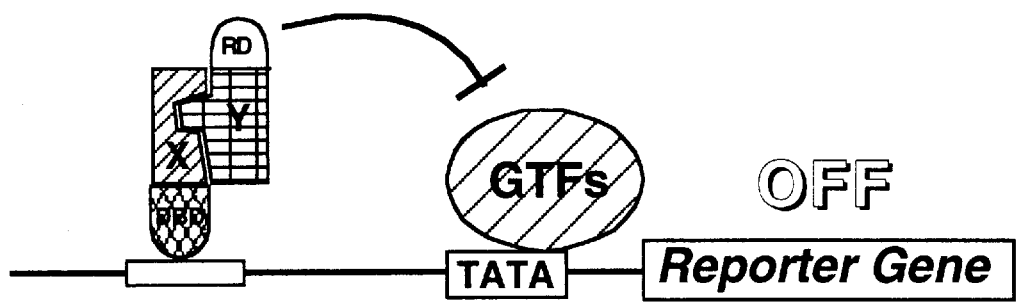

One embodiment of the RTA is illustrated in FIG. 1. The bait protein of interest, which is capable of activating transcription, is fused to a DNA-binding domain. The DNA-binding domain-bait fusion is then expressed in a cell containing a reporter gene which has upstream binding sites for the DNA-binding domain. When expressed on its own the bait fusion should activate reporter gene transcription. The prey protein is fused to a transcriptional repression domain, such as the TUP1 repression domain. When expressed in the same cell as the bait fusion, specific interaction between the bait and prey fusion proteins brings the repression domain into proximity with the reporter gene promoter and causes inhibition of transcription. Specific interaction between the bait and prey fusion proteins can therefore be detected by assaying for reduced expression of the reporter gene. Various reporters may be used, for example beta-galactosidase activity produced by the LacZ reporter gene. Activity of the reporter gene may also be determined by directly analysing the amount of mRNA transcribed from the reporter gene.

Counterselectable Reporter Genes for Detection of Transcriptional Repression

Because protein-protein interaction in the RTA system causes inhibition of transcription, genetic selection of cells exhibiting specific protein-protein interactions using the RTA system may be accomplished with reporter genes whose expression can be selected against, or counterselected. Particular counterselectable genes are disclosed herein by way of example to illustrate the properties of such genes; those skilled in this art will understand that the RTA system of the invention may be used with other counterselectable reporter genes.

A number of genes that have been used for counterselection strategies in Saccharomyces, as summarized in Table 1 may be used in this invention. Preferably the counterselectable gene used will be URA3, CAN1 or the GAL1 genes (as described in Table 1).

TABLE 1

Counterselectable Markers in Yeast

| Gene | Product | Phenotype of Null Mutation | Counterselection | Ref. |
|------|---------|---------------------------|------------------|------|
| URA3 | Orotidine-5'-decarboxylase | Unable to grow in the absence of uracil. Resistant to 5-FOA. | URA3$^+$ yeast cannot grow in the presence of 5-FOA. | (5) |
| CAN1 | Arginine permease | Resistant to canavanine. | CAN1$^+$ yeast cannot grow in the presence of canavanine. | (21) |
| GAL1 | Galactokinase | Unable to use galactose. Resistant to 2-deoxygalactose. | GAL1$^+$ yeast cannot grow in the presence of 2-deoxygalactose. | (22) |
| LYS2 | a-aminoadipate reductase. | Require lysine for growth. Resistant to a-aminoadipate. | LYS2+ yeast cannot grow on media containing a-aminoadipate as the sole source of nitrogen. | (9) |
| CYH2 | L29 ribosomal protein. | Lethal, but a CYH2 point mutation confers resistance to cycloheximide. | CYH2$^+$ yeast cannot grow on cycloheximide. | (24) |
| MET15 | O-acetylhomoserine sulfhydrylase | Methionine auxotrophy. | MET15$^+$ yeast are sensitive to methyl mercury. | (41) |

The URA3 gene encodes orotidine decarboxylase, which is required for de novo biosynthesis of pyrimidine nucleotides. Yeast cells lacking ura3 require uracil to grow. 5-flourootic acid (5-FOA) is a pyrimidine analog which is converted to 5-flourouracil by the action of orotidylate decarboxylase (URA3). 5-flourouracil is very toxic to yeast cells and therefore cells which express URA3 cannot grow in the presence of 5-FOA, providing a counterselection for URA3 expression.

The CAN1 gene encodes a membrane arginine transporter protein. Cells that can synthesize arginine de novo do not need the CAN1 enzyme to grow. Canavanine is a toxic arginine analog which can be transported into the cell by the CAN1 membrane arginine transporter protein. Therefore, cells which produce CAN1 cannot grow in the presence of canavanine because the toxic substance becomes transported into the cell.

The GAL1 gene encodes the galactokinase which produces galactose-1-phosphate from galactose; this is the first reaction in the pathway which converts galactose into glucose. The galactose analog 2-deoxygalactose is converted by GAL1 into the toxic substance 2-deoxygalactose-1-phosphate which accumulates because it cannot be used by downstream enzymes in galactose catabolism. Cells that express GAL1 cannot grow on 2-deoxygalactose.

Repression of URA3, CAN1 and GAL1 gene transcription can be detected by the ability of cells to grow in the presence of 5-FOA, canavanine, and 2-deoxygalactose, respectively.

Components for Performing Genetic Screens with the RTA System

1) RTA Hosts

Cells used for the RTA assay will typically be transformed with vectors carrying the bait and prey fusion is protein genes. To enable selection of transformed cells, cells for performing RTA genetic screens may advantageously have mutations in the genes which are used as selectable markers on such plasmids. Additionally, the strain may have reporter genes, such as counterselectable genes, which can be used for selection of RTA interactions.

In yeast cells for example, GAL4 DBD bait expression plasmids may be used with a TRP1 marker, and TUP1 prey expression plasmids may be used with either a HIS3 or LEU2 marker. In such an embodiment, selection of the bait and prey plasmids is facilitated in host strains that lack such functions, designated trp1$^-$, his3$^-$, or leu2$^-$. The strain may also be can1$^-$ and ura3$^-$ to enable use of the CAN1 and URA3 genes as reporters for the RTA assay. In embodiments in which GAL4's DNA-binding domain is used for the bait fusion proteins, the yeast strain should also be gal4$^-$ so that expression of the reporter genes is solely dependent upon the GAL4-transactivator bait fusion. In summary, such a yeast strain may have the genetic background trp1, his3, ura3, can1, and bear combinations of integrated URA3, CAN1 and LacZ reporter genes under the control of promoters bearing binding sites for GAL4 (see below). The endogenous wild type GAL1 gene can also be used for the genetic screen by counterselection with 2-deoxygalactose.

2) Reporter Genes

Host cells for RTA system assays may include reporter genes having promoters with binding sites for the DNA-binding domain of the bait fusion protein that will be used. Alternatively, such reporter genes may be introduced transiently into host cells on vectors for the purpose of conducting the RTA assay.

Figure 5:
FIGS. 5A–5D: Schematic representation of reporter genes used for the unmodified repressed trans-activator system.
Figure 5:
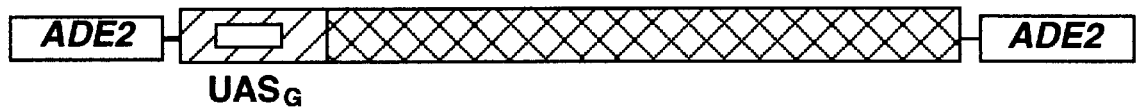
Figure 5:
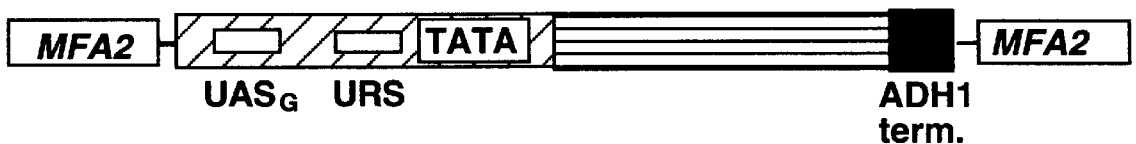
Figure 5:

In one embodiment, genetic selection of yeast strains exhibiting specific protein-protein interactions in an RTA assay may be genetically selected using counter-selectable reporter genes under the control of promoters with binding sites for GAL4. In one such embodiment, the GAL1-URA3 reporter gene is constructed such that its natural upstream regulatory sequences have been replaced with the upstream activation sequence (UAS) from the GAL1 promoter, which contains four strong binding sites for GAL4 protein (35). The GAL1-LacZ and GAL1-CAN1 reporter genes may comprise the GAL1 promoter, including the UAS and URS, the TATA-element, and the coding sequence for the first few amino acids of GAL1 protein fused in-frame with the E. coli LacZ gene or the CAN1 gene, respectively (see FIG. 5). Since the LacZ gene is derived from E. coli and does not contain a signal for polyadenylation of transcripts, a transcriptional termination sequence derived from the yeast ADH1 gene may be inserted following the LacZ coding sequence (FIG. 5).

Reporter genes may be integrated into host yeast strains by homologous recombination using the standard "two-step" technique, which eliminates flanking DNA duplications to ensure their stability (40). This is accomplished as follows. The reporter genes are inserted into the integration locus gene on plasmids which also contain the URA3 marker. Reporter plasmids are linearized using a restriction endonuclease which cuts within the integration gene. The linearized DNA is transformed into ura3$^-$ yeast, and the transformed yeast are plated on minimal medium lacking uracil to select for plasmid integrants. URA$^+$ transformants are then grown non-selectively for several generations and plated on 5-FOA to select for loss of the URA3 gene by recombination. A proportion of the 5-FOA-resistant yeast colonies will retain the reporter gene integrated at the defined locus; the remaining colonies will typically have lost the integrating plasmid entirely. Reporter gene transformants can be identified by Southern blot analysis of genomic yeast DNA. By this technique, yeast strains can be constructed which have multiple reporter genes without the loss of selectable markers. The GAL1-URA3 fusion gene is integrated into the yeast chromosome at the ADE2 locus, the GAL1-CAN1 is integrated at the LYS2 locus, and the GAL1-LacZ fusion is integrated at MFA2 (see Table 2, and FIG. 5).

TABLE 2

Expression plasmids and reporter genes for RTA

| Expression Plasmid | Selection Marker | Plasmid Name | Notes |
|---|---|---|---|
| GAL4 Bait Expression Plasmids | TRP1 | pG1, pG2, pG3 | Single copy plasmid vectors for low-level expression of GAL4 bait fusions. |
| GAL4 Bait Expression Plasmids | TRP1 | pY1, pY2, pY3 | Single copy plasmid vectors for moderate-level expression of GAL4 bait fusions. |
| TUP1 Prey Expression Plasmids | HIS3 | pBDH1, pBDH2, pBDH3 | Multicopy vectors with HIS3 selection for expression of TUP1 prey fusions. |
| TUP1 Prey Expression Plasmids | LEU2 | pBDL1, pBDL2, pBDL3 | Multicopy vectors with LEU2 selection for expression of TUP1 prey fusions. |

| Reporter Gene | Integration Locus | Plasmid Name | Notes |
|---|---|---|---|
| GAL1 | GAL1 | none | Endogenous GAL1 gene. Counterselection with 2-deoxygalactose. |
| GAL1-URA3 | ADE2 | pGU | Counterselection with 5-FOA, positive selection on medium lacking uracil. |
| GAL1-LacZ | MFA2 | pGL | Produces blue colonies on X-gal when active and white colonies on X-gal when repressed. |
| GAL1-CAN1 | LYS2 | pGC | Counterselection with canavanine. |
| H-GAL1-URA3 | ADE2 | pHGU | Identical to the GAL-URA3 reporter except that a single binding site for GCN4 has been inserted upstream of the GAL4 binding sites. For use with non-activator as well as activator baits. |
| H-GAL1-LacZ | MFA2 | pHGL | Identical to the GAL-LacZ reporter except that a single binding site for GCN4 has been inserted upstream of the GAL4 binding sites. For use with non-activator as well as activator baits. |
| H-GAL1-CAN1 | LYS2 | pHGC | Identical to the GAL-CAN1 reporter except that a single binding site for GCN4 has been inserted upstream of the GAL4 binding sites. For use with non-activator as well as activator baits. |
| GAL1-HIS3 | LYS2 | pBM1499 | For use in measuring inhibition of protein-protein interactions and genome-wide protein interaction strategies. |

3) Bait Expression Plasmids

Vectors for expressing the bait fusion protein having a DNA-binding domain may comprise an insertion site in-frame with a sequence coding for the DNA-binding domain. Insertions at such an insertion site will permit expression of a bait fusion protein having the DNA-binding domain.

Figure 2:
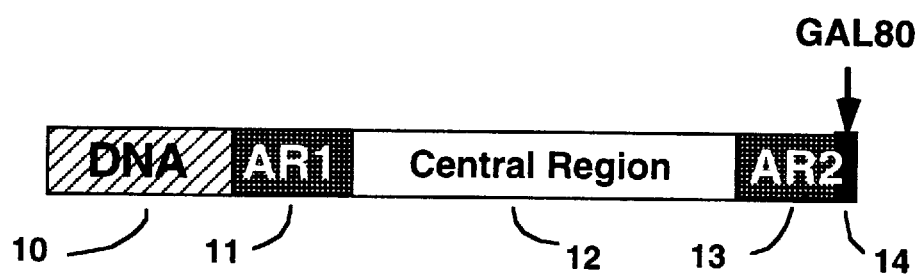
FIG. 2: Schematic representation of the GAL4 protein. The N-terminal 147 amino acids contain the DNA-binding domain 10, which binds specifically to 17 base pair sequences within the $UAS_G$. Transcriptional activation is mediated by Activating Region 1 11 and Activating Region 2 13. The central region 12 residing between the two activating regions is necessary for inhibition of GAL4 activity in the presence of glucose. The negative regulatory protein GAL80 makes primary contact with the C-terminal 30 amino acid residues of GAL4 protein 14.
Figure 3:
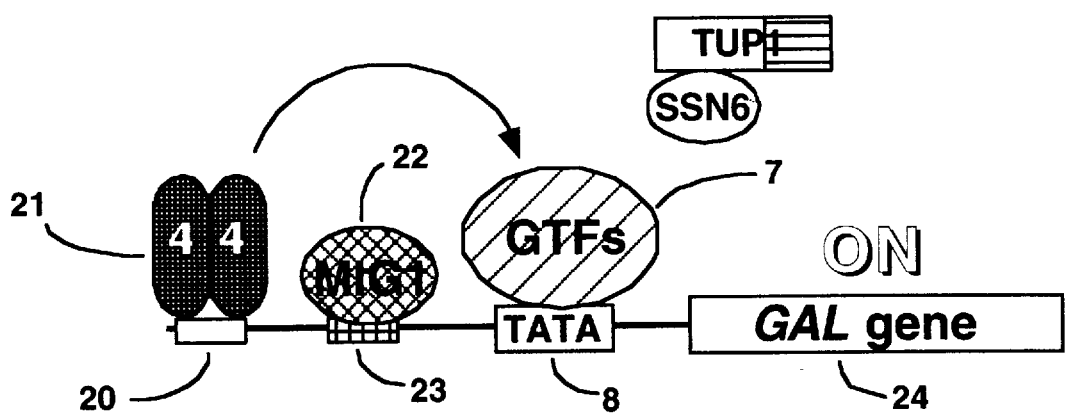
FIGS. 3A–3B: Function of TUP1 protein in glucose repression of the GAL genes. Schematic representation of a typical GAL gene in Saccharomyces.
Figure 3:
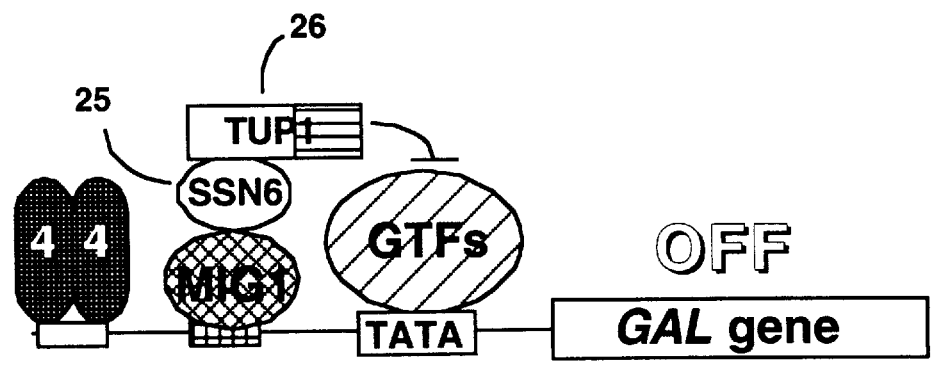
Figure 4:
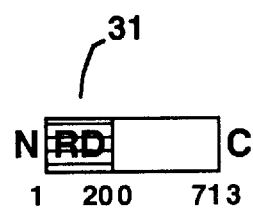
FIGS. 4A–4B: Identification of a transcriptional repression domain on the TUP1 protein.
Figure 4:
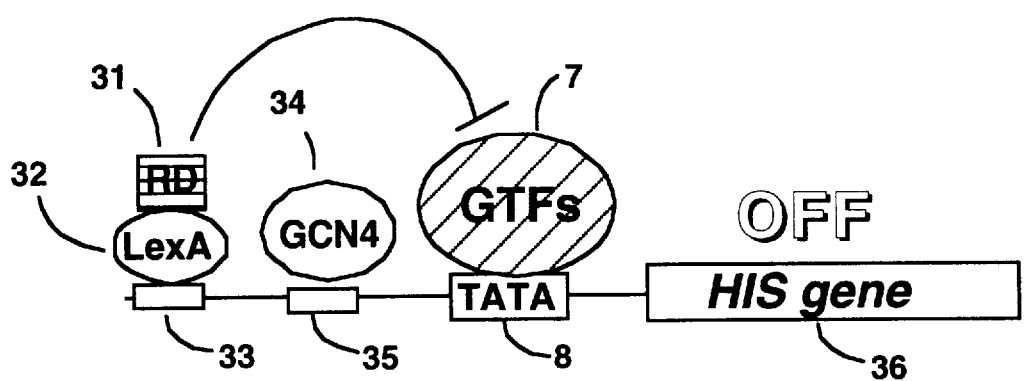

In one embodiment, bait fusion proteins for RTA genetic screens may be constructed as fusions with the N-terminal 147 amino acids of GAL4. This portion of GAL4 comprises the DNA-binding domain (see FIG. 2). This DNA-binding domain binds to 17 base pair elements within the upstream activating sequence for galactose, but does not activate transcription. For the RTA system, this DNA-binding domain may be fused to a heterologous amino acid sequence having a transcription activating domain. An alternative DNA-binding domain is the DNA-binding domain of the $E.$ $coli$ LexA protein.

Figure 6:
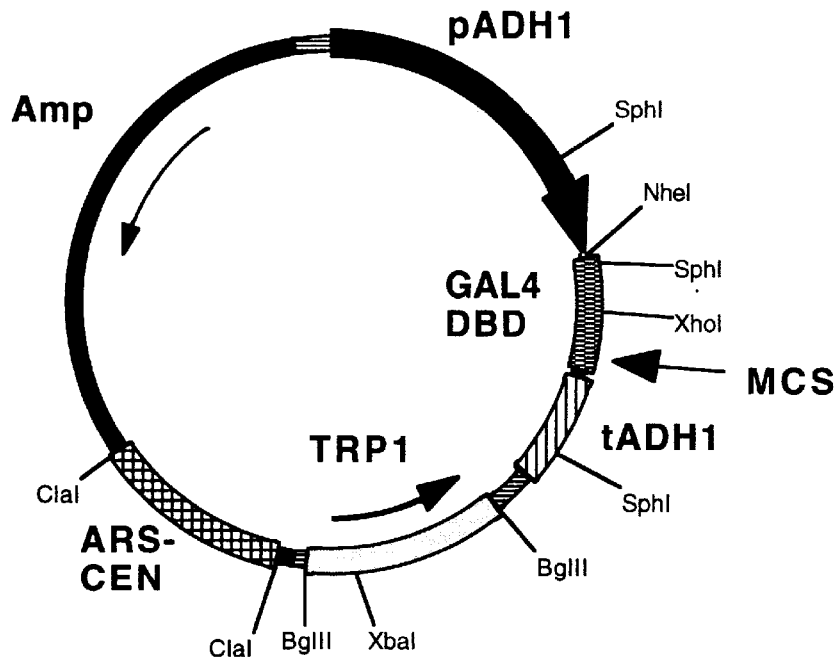
FIGS. 6A–6B. Schematic representation of GAL4-bait expression plasmids for the repressed trans-activator system.
Figure 6:
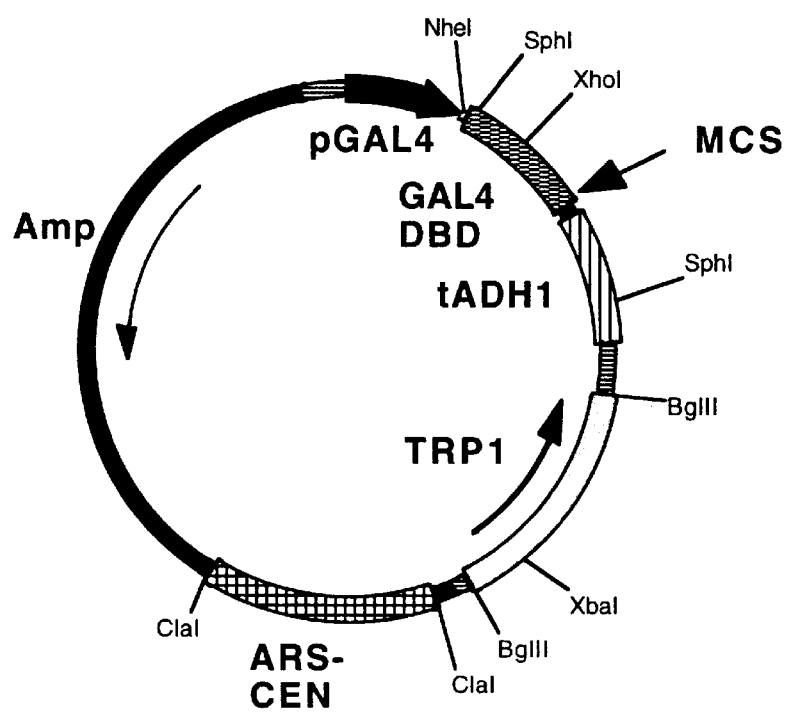

The sensitivity of the RTA assay may vary depending on the level of bait expression. To produce embodiments of the RTA having different levels of bait expression, plasmids may be constructed that express the GAL4-bait at various levels. For example, the pY1, pY2 and pY3 plasmids disclosed herein are ARS-CEN vectors which are maintained at a single copy per yeast cell (36). These plasmids use the ADH1 promoter to express the GAL4-DNA binding domain fusions. The pY plasmids produce moderate to high levels of GAL4 DBD-bait fusion expression. Also disclosed are the pG1, pG2, and pG3 plasmids that may enable expression of lower levels of bait fusion. These plasmids are identical to the pY vectors except that the GAL4 DBD-bait fusions are expressed from GAL4's own weak promoter (FIG. 6). Both sets of plasmids have the TRP1 gene to enable selection and maintenance in the trp1⁻ yeast strain. The 1, 2, and 3 numbered pY and pG vectors have the multiple cloning (insertion) site following the GAL4 DNA-binding domain coding sequence staggered by a single nucleotide to facilitate construction of in-frame fusions. The multiple cloning sites are immediately followed by translational stop codons in all three reading frames, and the transcriptional termination sequence from the ADH1 promoter (FIG. 6, (36)).

4) Prey Vectors and Libraries

To construct a vector coding for a prey fusion protein, an amino acid sequence of interest may be inserted in-frame into a coding sequence for a transcriptional repressor domain. Expression of the recombinant gene produces the prey fusion protein having a transcriptional repressor domain and the amino acid sequence of interest for the RTA assay. The position of the repressor domain may vary. Some repressor domains may function at the C-terminal of the fusion protein, others may function at the N-terminal. Prospective repressor domains may be assayed for function as part of a fusion protein as disclosed below in the "Examples" section for the TUP1 repressor domain.

Certain repressor domains may exert their effect through interaction with specific parts of the transcriptional machinery. For example, the holoenzyme-associated cyclin-dependent protein kinase SRB10 is required for repression of transcription by TUP1 (48). As set out below in the "Examples" section, the TUP1 repressor domain may not function in srb10⁻ strains. Assays similar to the assay disclosed in the "Examples" section may be performed to determine whether other repressor domains have similar requirements for interaction with specific parts of the transcriptional apparatus.

In one embodiment, to vary the sensitivity of detection of specific RTA interactions, the prey fusion protein may advantageously be expressed at a higher level than the bait fusion protein. In one such embodiment of the invention, the TUP1-prey expression plasmid may comprise the 2 micron circle (2 μ) replication sequence which replicates at 40–100 copies per yeast cell. In such an embodiment, the prey fusion proteins are generally over expressed relative to the bait fusion proteins.

Figure 7:
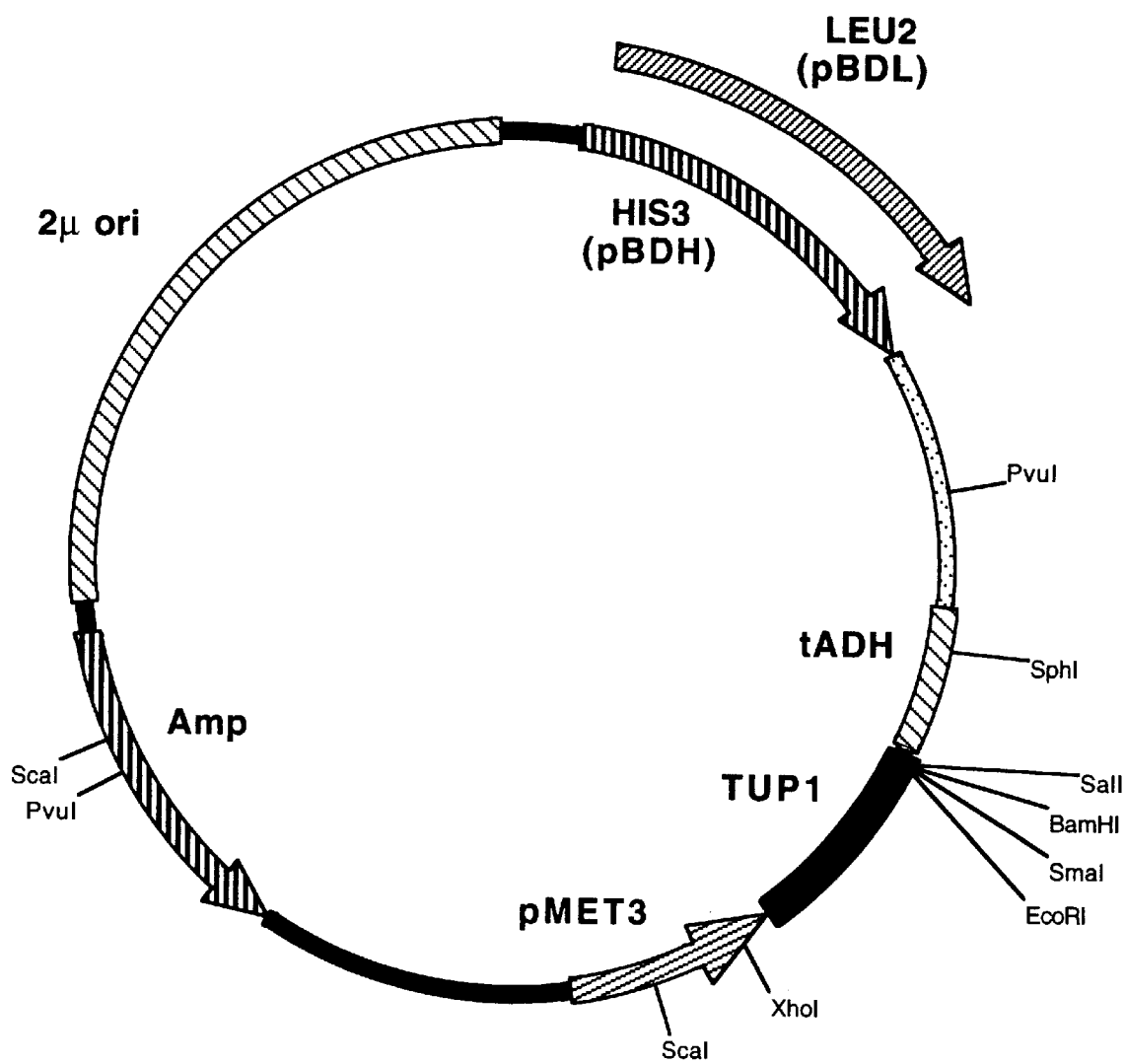
FIG. 7: Schematic representation of the TUP1-prey expression vectors for the repressed trans-activator system. The TUP1 prey expression plasmids are 2 micron origin vectors ($2\mu$ ori), in which the MET3 promoter (pMET3) is used to express the TUP1 repression domain (TUP1). TUP1 is immediately followed by the restriction endonuclease sites as indicated. TUP1-prey transcripts are terminated by the ADH1 terminator (tADH). The PBDH plasmids contain the HIS3 gene, while the pBDL plasmids (not shown) contain the LEU2 gene for selection in yeast. The 1, 2 and 3-numbered pBDH and PBDL plasmids (not shown) are identical except that the multiple cloning sites are staggered by a single nucleotide relative to each other to simplify construction of in-frame fusions, and facilitate library construction.
Figure 8:
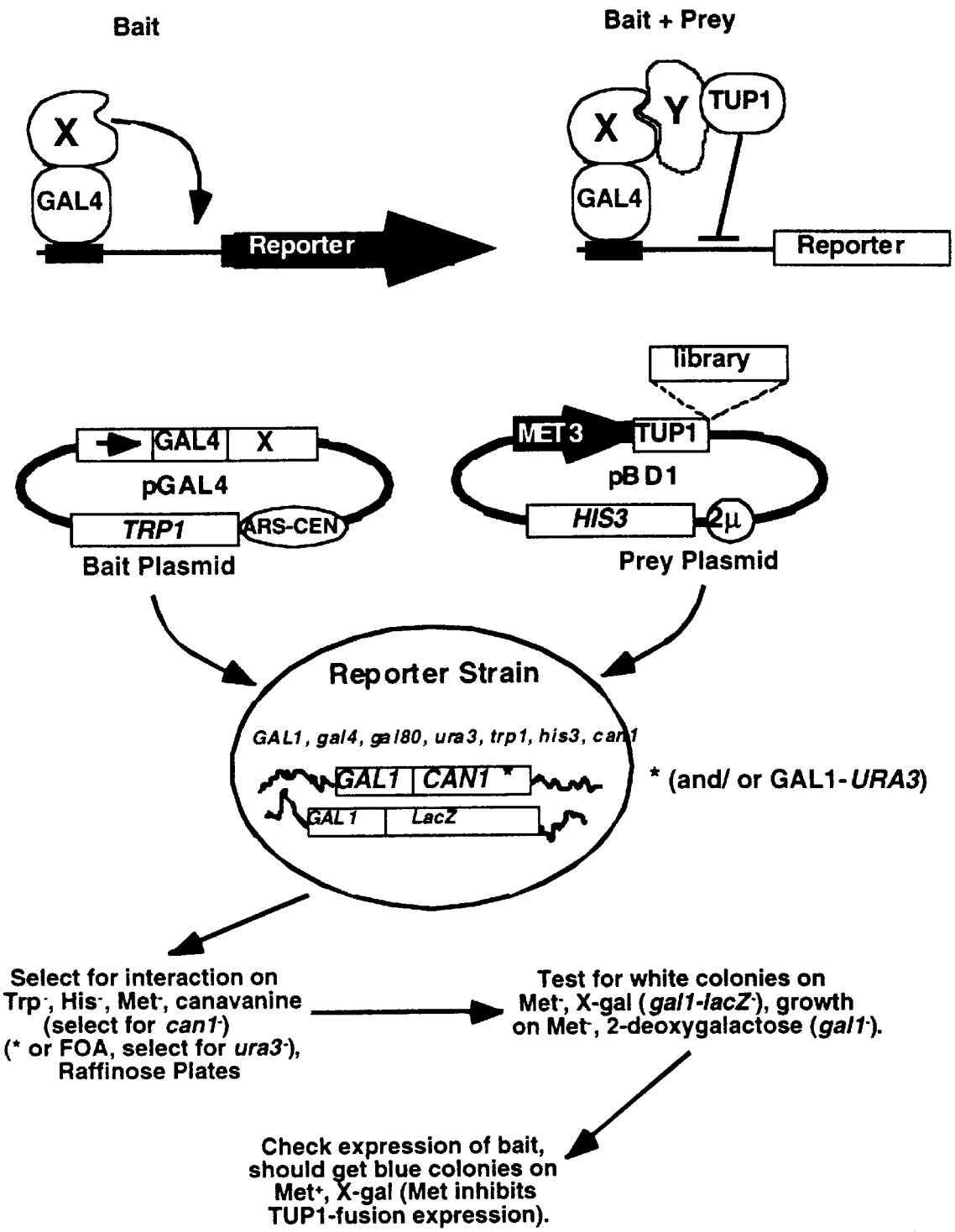
FIG. 8: Flow diagram illustrating a strategy for screening libraries for novel protein-protein interactions using the unmodified form of the repressed trans activator system. In the example shown the pBDH-derived library is used, which requires his⁻ selection; a screen using a pBDL-derived library is identical except that selection for library transformants would use leu⁻ medium.

The gene for the prey fusion protein may advantageously be placed under the control of repressable promoter. In one embodiment, the prey fusion vectors (PBDH and PBDL, see FIG. 7) may contain the MET3 promoter for expression of the TUP1-prey fusions. The MET3 promoter is repressed in yeast growing in methionine (11). For confirmation of protein-protein interactions identified by genetic screens using RTA, it may be advantageous to repress expression of the TUP1-prey fusion after initial selection to ensure that the GAL4-bait fusion has not lost its ability to activate transcription (see below). The MET3 promoter may be fused upstream of the coding sequence for the N-terminal repression domain of TUP1 (amino acids 1–200), which may be followed immediately by a multiple cloning site (see FIG. 7). The pBDH and pBDL plasmids numbered 1, 2 and 3 have the multiple cloning site staggered by a single nucleotide to increase the probability of generating in-frame fusions with inserts of random DNA and cDNA fragments. Transcripts from the MET3 promoter are terminated by the ADH1 terminator. In this embodiment, the pBDH TUP1-bait expression vectors have the HIS3 gene, which allows for selection and maintenance in his3− yeast strains, while the pBDL plasmids are identical except that the selectable marker is LEU2.

The PBDH and pBDL plasmids may be used to insert previously cloned DNA fragments for characterization of known or suspected protein-protein interactions. The plasmids are also designed for construction of cDNA libraries from tissues or organisms which have a high proportion of spliced transcripts, or genomic libraries for lower eukaryotes and prokaryotes which have few introns.

Genomic libraries for organisms such as Saccharomyces, may be prepared by performing a partial digestion of genomic DNA with the endonuclease Sau3AI to generate a population of fragments within a desired size range, for example 400 to 1000 nucleotides on average. The randomly digested DNA may then be ligated to a pool of the three pBDH or pBDL plasmids digested with BamHI, which generates ends that are compatible with Sau3AI. Since the cloning sites in the PBDH and pBDL vectors are staggered by a single nucleotide, in theory, every partially digested genomic fragment should be represented by in-frame fusions within the library. cDNA libraries may be prepared from mRNA extracted from the tissue, cell type, or species of interest. In constructing cDNA libraries, a directional cloning strategy (26) may be used so that the cDNA inserts are expressed in the sense orientation relative to the TUP1 coding sequence. cDNA may be prepared from polyadenylated mRNA, purified by affinity with oligo dT, and reverse transcribed with random primers containing a 5′ BamHI linker, using 5-methyl-cytidine triphosphate in the reaction. Second-strand cDNA synthesis may then be carried out normally following digestion with RNAse H. The 5′ end of the cDNA may be made blunt with S1 nuclease, and the cDNA fragments ligated to an EcoRI linker. The linkers on the ends of the cDNAs may then be digested with EcoRI and BamHI; incorporation of 5-methyl-cytidine in the initial reverse transcription reaction guards against digestion of internal EcoRI and BamHI sites. The cDNA fragments may then be cloned into a pool of the three pBDH or pBDL plasmids which have been digested with EcoRI and BamHI.

To simplify construction of large representative TUP1-cDNA fusion libraries, the pBDH and pBDL plasmids may be inserted into lambda phage replacement vectors such that the plasmid is flanked by loxP sites, the target cis-element for Cre recombinase. Once cDNA has been cloned into the lambda vectors, the entire library may be released as plasmids by infection of the phage library into *E. coli* cells expressing Cre recombinase (8).

RTA Genetic Screen

To identify amino acid sequences that interact with a transcriptional activator amino acid sequence of interest, an appropriate host cell may be cotransformed with a gene for the bait fusion protein having the transcriptional activator sequence and with a gene for the prey fusion protein having the transcriptional repressor domain.

In one embodiment, a yeast strain bearing the GAL4-responsive reporter genes is transformed with a GAL4-bait transactivator expression plasmid (constructed in either the pY or the pG vectors); transformants which take up and express the GAL4-bait expression plasmid can be identified by growth on medium lacking tryptophan. The GAL4-bait transactivator fusion expressed in TRP+ transformants should cause expression of the GAL4-responsive reporter genes such that they form blue colonies on medium containing X-gal, a chromogenic substrate for beta-galactosidase produced by the LacZ gene. Activation of the reporter genes should also render the strain incapable of growth on 5-FOA, 2-deoxygalactose, and canavanine. The tester yeast strain transformed with the GAL4-bait expression plasmid should also be capable of growing on medium lacking uracil, because the GAL4-transactivator bait will cause expression of URA3.

The yeast strain expressing the bait fusion protein may be transformed with a plasmid library constructed in the pBDH or PBDL vectors; the library transformants may be selected on agar plates lacking tryptophan and histidine or leucine, respectively. Colonies from the library transformation may be scraped into minimal medium containing 25% glycerol, the cell suspension may then be pooled and stored frozen as aliquots in liquid nitrogen.

To select for TUP1-prey fusion proteins that interact with the GAL4-bait fusion proteins, the library transformants may be thawed and plated on medium which selects for repression of the GAL4-responsive reporter genes. Library transformants may initially be selected for clones that cause growth on canavanine, indicating repression of the GAL1-CAN1 reporter gene. Clones which grow on canavanine may then be tested for growth on 5-FOA and 2-deoxygalactose. Repression of the GAL1-LacZ reporter gene should also cause formation of white colonies on X-gal plates.

Repression of the reporter genes could be caused by: a) an RTA interaction between the GAL4-bait transcriptional activator and the TUP1-cDNA fusion such that the TUP1 transcriptional repression domain inhibits reporter gene expression; or b) could result from loss of expression of the GAL4-bait fusion because of a mutation in the bait expression plasmid. The use of four different reporter genes in such a screen greatly reduces the likelihood that growth under the counterselectable conditions could be caused by mutations of the reporter genes. Therefore, to distinguish between the likely possibilities, clones in which all of the reporter genes are repressed may be grown on agar plates containing methionine to inhibit expression of the TUP1-prey fusions, because of the MET3 promoter. On methionine-containing medium the GAL4-bait fusion should be free to activate transcription because the TUP1-prey fusion will not be expressed. This can be confirmed by transferring colonies to X-gal plates which contain or lack methionine. Clones which produce TUP1-prey fusions that interact with the GAL4-bait, and in which the Ad GAL4-bait is intact, should form blue colonies on X-gal plates containing methionine, but white colonies on X-gal without methionine.

Further control assays may be carried out to demonstrate that the TUP1-prey fusion interacts specifically with the bait of interest and does not cause repression of transcription by interaction with the DNA-binding domain of GAL4, or other proteins that may bind upstream of the reporter genes. This may be performed, for example, by transforming the recovered TUP1-prey expression plasmid into a yeast strain expressing an unrelated GAL4 DBD-transactivator bait fusion protein.

Plasmid clones identified by the foregoing tests may be extracted from yeast and recovered by transformation into *E. coli*. Plasmid DNAs may be sequenced using oligonucleotide primers flanking the pBDH and PBDL cloning sites.

Modification of the RTA System to Detect Protein-Protein Interactions with Non-Transactivators Several modifications can be made to the RTA system to enable detection of protein-protein interactions involving bait fusion proteins that do not activate transcription. This provides additional flexibility to the system because the interactions of an amino acid sequence of interest may be assayed whether or not such a sequence activates transcription.

a) Modification of the reporter genes

One embodiment of RTA for use with non-transactivating amino acid sequences involves modification of the reporter genes such that they have an upstream element responsive to a transactivator protein (i.e. a transactivator protein that is not the bait fusion protein). The reporter genes for assaying the interactions of amino acid sequences that are not transcriptional activators may be identical to the GAL1-CAN1, GAL1-URA3, and GAL1-LacZ reporters described above (FIG. 5), except that the promoters for such reporter genes further comprise a binding site for an additional transcriptional activator. In one embodiment, such a binding site may be inserted in the promoter upstream of the $UAS_G$ which contains the GAL4 binding sites (see Table 2).

In one embodiment, GCN4 may be used as the transcriptional activator for the reporter genes. GCN4 is normally involved in activating transcription of genes required for synthesis of histidine, and binds to elements within the upstream activating sequence for the HIS genes ($UAS_H$). Where there is a GCN4 binding site in the promoters of the reporter genes, in the absence of interaction between the prey repressor fusion protein, such as the TUP1-prey, and the DNA-binding bait fusion protein, such as the GAL-4 bait, GCN4 will cause constitutive expression of the reporter genes, such as H-GAL1-CAN1, H-GAL1-URA3, and H-GAL1-LacZ, such that the yeast strain will form blue colonies on X-gal and will be incapable of growing on canavanine or 5-FOA. However, an interaction between the prey and bait fusions will bring the repression domain into the vicinity of the promoter and inhibit reporter gene transcription.

b) Modification of the bait fusion vectors

Alternative embodiments of the invention may be used to assay the interactions of fusion proteins comprising heterologous non-transactivator amino acid sequences. One such embodiment comprises modified vectors in which the bait fusion protein itself possesses transactivating activity. In one aspect of the invention, the transactivating activity may be provided by using amino acids 1–238 of GAL4 to make the bait fusion protein (rather than only using DNA binding domain amino acids 1–147 of GAL4). GAL4 amino acids 148–238 contains activating region 1 (see FIG. 2). Hybrid proteins produced by fusing baits of interest to GAL4 (1–238) may activate transcription because of the presence of the GAL4 activating region. A tripartite bait fusion protein consisting of the GAL4 DNA-binding domain, GAL4 activating region 1, and the protein fragment of interest may be used to screen libraries with the standard GAL1-CAN1, GAL1-URA3, and GAL1-LacZ reporters as described above. A caveat to this strategy is that proteins which interact with activating region 1 to mask its activating function may produce a positive result in an RTA assay, as well as those proteins which specifically interact with the bait. As mentioned above for the standard RTA assay, clones expressing bait fusions which cause repression of the reporter genes may be tested for specificity towards the bait. In the embodiment of RTA that uses GAL(1–238) fusion proteins as bait, potentially positive prey clones may be retransformed into a strain expressing GAL4(1–238) without a heterologous amino acid sequence fusion, to distinguish between prey fusions that interact with the heterologous amino acid sequence in the bait fusion from those that interact with GAL4's DNA binding domain or activating region 1.

Adaptations of the RTA System for other cells

Transcriptional repressors similar to Saccharomyces TUP1 protein have been identified in cells of other eukaryotes (19), including WT1, verbA, Egr-1, YY1, AdE1B, E4B4, SCIP, kid-1, Znf2 and kox-1 (see Table 7, ref. 35). The RTA system of the invention may be carried out in any such cells in which appropriate components of the system are available: repressor domains for prey fusion proteins, DNA-binding domains for bait fusion proteins and reporter genes for detecting interaction between the bait and prey fusion proteins.

Figure 9:
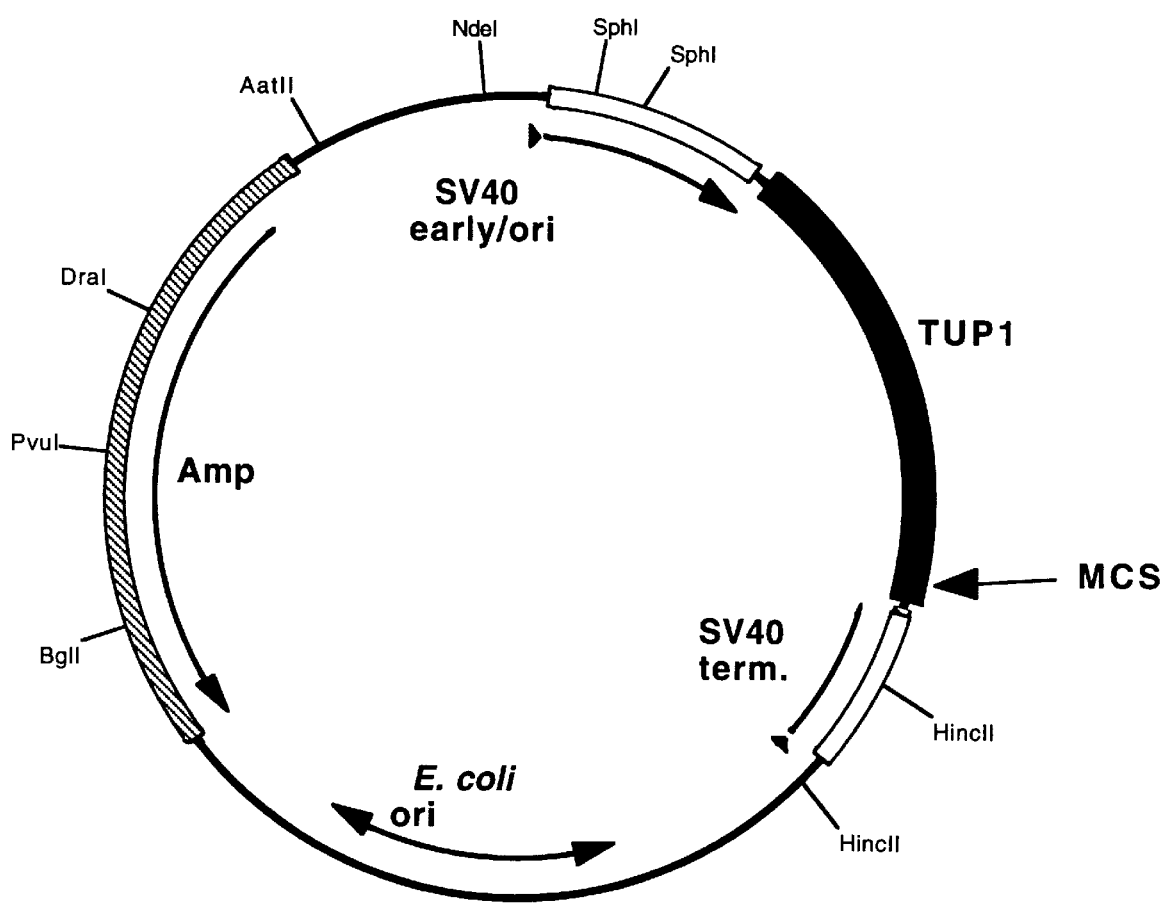
FIG. 9. Schematic representation of mammalian pT TUP1-prey expression vectors for performing the RTA system in mammalian cells. The pT plasmids employ the SV40 early promoter region (SV40 early/ori) for expression of the N-terminal repression domain of TUP1. The TUP1 coding sequence is immediately followed by a multiple cloning site which is identical to the pM plasmids (36). TUP1-prey transcripts are terminated within by the SV40 polyadenylation signal (SV40 term.). The pT1, pT2, and pT3 plasmids are identical, except for the reading frame of the multiple cloning sites.

The RTA system can be adapted for use in mammalian cells to characterize protein-protein interactions with transactivators, and non-transactivators, for which molecular clones are available. In one embodiment, GAL4 transactivator bait fusions can be constructed using the mammalian expression plasmids pM1, pM2 and pM3 (36). The relevant features of these plasmids include: the strong SV40 early region promoter, which directs expression of the GAL4-DBD fusions; a multiple cloning site, which is staggered by a single nucleotide in the 1, 2, and 3 numbered plasmids to simplify construction of in-frame fusions; translational termination codons in all three frames following the cloning sites; and a transcriptional termination signal from SV40 virus immediately following the translational stop codons. Similar vectors may be constructed for expression of TUP1 fusion prey fusions in mammalian cells, called pT1, pT2, and pT3 (see FIG. 9).

A variety of different reporter genes have been described for use in mammalian cells, and can be used to measure transactivation by bait fusions and the repressive effect of an RTA interaction between bait and prey fusion proteins. In one embodiment, the plasmid pG5EC has a minimal promoter consisting of 5 GAL4 sites inserted immediately upstream of the Adenovirus E1B TATA-box element and the bacterial chloramphenicol acetyl transferase (CAT) gene (36). Similarly, the plasmid pG5tkCAT has 5 GAL4 binding sites upstream of a truncated derivative of the Herpes virus thymidine kinase (tk) gene. CAT enzyme activity may be detected in extracts of cells, facilitating measurement of expression of the reporter genes. When transfected into mammalian cells, the pG5EC reporter gene produces negligible CAT activity unless co-transfected with a plasmid that produces a GAL4-bait transactivator fusion. In contrast, the pG5tkCAT reporter produces a small amount of CAT activity on its own, due to the remaining cis-acting elements within the tk promoter. Co-transfection of a GAL4-bait transactivator expression plasmid causes significantly elevated CAT activity generated by the pG5tkCAT reporter.

To measure interaction between bait and prey fusion proteins, the reporter gene plasmid may be co-transfected into mammalian cells with both the bait and prey expression plasmids. In one embodiment, interaction between the two fusion proteins may be detected by decreased production of CAT activity caused by the TUP1-prey fusion relative to a control sample in which the GAL4-bait fusion expression plasmid is co-transfected with the parent TUP1 expression plasmid without an insert. An advantage of using the pG5tkCAT reporter gene construct is that the bait fusion does not necessarily have to activate transcription on its own. Interaction of the GAL4-bait with the TUP1-prey should cause a decrease in the elevated basal transcription of this reporter gene.

Known reporter genes other than CAT may be used for RTA in mammalian cells as well. These include the firefly luciferase, secreted alkaline phosphatase (SEAP) (4), beta-galactosidase (lacZ) (20), the green or blue fluorescing proteins (GFP, BFP) (1), or cell surface markers such has hemaglutinin (HA), or CD2 (13). Some of these reporter genes may be more useful for applications involving automated detection methods than is the CAT gene.

Modifications may be made to the mammalian RTA system that would allow screening of libraries for novel interacting proteins in mammalian cells. A mammalian cell standard two-hybrid assay has been described which may allow library screening (49). Such a screening system may be adapted for RTA assay by selection of appropriate repressor and DNA-bind domains for the fusion proteins, and adoption of appropriate marker genes in accordance with the present disclosure.

Use of the RTA System for Identification and Characterization of Specific Protein-Protein Interaction Inhibitors The RTA system of the invention may be adapted for use in screening and characterizing specific inhibitors of protein-protein interactions. An inhibitor may be any small z molecular compound, lipid, peptide, polypeptide, or nucleic acid which can be delivered to the test system by expression or exogenous addition. The RTA system may be adapted for use in a variety of cells, including yeast or mammalian cells, for screening inhibitors of protein-protein interactions.

Figure 10:
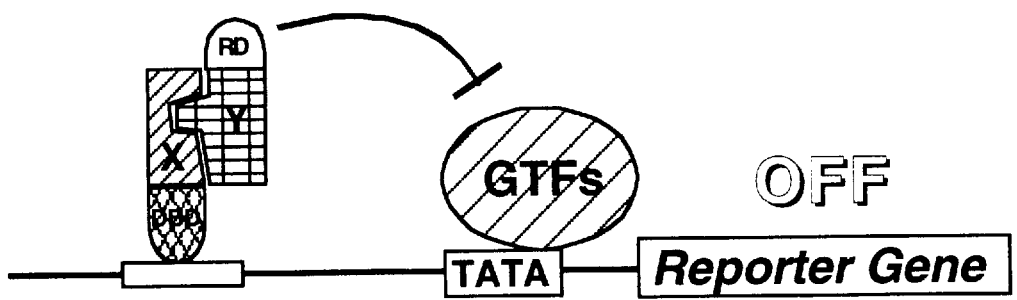
FIGS. 10A–10B: Schematic representation of the use of the RTA system for assaying inhibitors of a specific protein-protein interaction.
Figure 10:
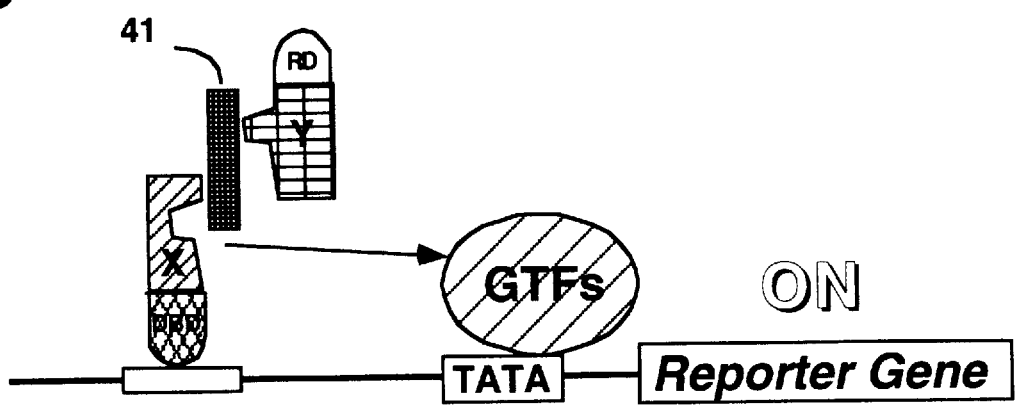

Because protein-protein interactions in the RTA system are detected by repression of a reporter gene, inhibition of interaction between the bait and prey fusions in the RTA system will cause induction of the reporter gene (see FIG. 10). This fundamental difference between the RTA and two-hybrid and interaction trap systems of the prior art provides an important advantage in assaying protein-protein interaction because inhibition results in a positive rather than a negative signal. The detection of a positive rather than a negative signal is advantageous because it tends to minimize false results, which may be obtained because some factor other than a specific interaction of interest has disrupted the assay system and caused a negative signal.

a) Assay of specific protein-protein interaction inhibitors

In one embodiment, inhibitors of a specific protein-protein interaction can be assayed by first constructing a yeast strain which expresses the bait and prey fusion proteins, such as GAL4 DBD -bait and the TUP1-prey fusions, representing the specific interaction of interest. Interaction between the bait and prey fusions will cause repression the reporter genes, such as the GAL4-dependent reporter genes. When a substance is added to the yeast which prevents interaction between the bait and prey fusion proteins, the bait fusion protein, such as a GAL4-bait fusion, will become free to activate transcription, resulting in expression of the reporter genes, such as GAL4-dependent reporter genes (see FIG. 10). If the GAL4-dependent reporter genes disclosed above are used, a specific inhibitor will cause the yeast strain to become sensitive to the presence of canavanine, 2-deoxygalactose and 5-FOA because the GAL-CAN1, endogenous GAL1, and GAL1-URA3 reporter genes will be expressed.

It may be useful in assaying for inhibitors to provide for a positive signal to indicate expression of the reporter gene(s). For example, a GAL1-HIS3 reporter gene may be used. Induction of the HIS3 gene allows growth in medium lacking histidine. In such an embodiment, the tester strain for assaying inhibitors of protein-protein interactions may contain both the GAL1-LacZ and GAL1-HIS3 reporter genes, and have a defective chromosomal his3 gene. Because the HIS3 gene is used as a reporter gene for this modification, the pBDL expression plasmids (see Table 2) may advantageously be used to produce the TUP1-prey fusions. With the combination of reporters in such a modified strain, inhibition of bait and prey interaction can be detected by growth on medium lacking histidine and by production of b-galactosidase from the LacZ gene, which can be measured enzymatically.

An additional modification of the RTA assay of the invention may be useful to discriminate between strong and weak inhibitors of bait and prey interaction. The histidine analog 3-aminotriazole (3-AT) is a competitive inhibitor of the HIS3 gene product. 3-AT added to the growth medium to cause a requirement for stronger expression of the HIS3 gene in order to overcome the 3-AT inhibitory effect. In certain embodiments, the level of HIS3 expression required for growth in the absence of histidine may be directly proportional to the concentration of 3-AT in the growth medium (23). The results of such an assay may be evaluated on the premise that stronger inhibitors of a specific interaction between the bait and prey fusion proteins should allow cell growth on higher concentrations of 3-AT.

b) Assay of protein-protein interaction inhibitors in mammalian cells

In accordance with an aspect of the invention, inhibitors of protein-protein interactions may be assayed in mammalian cells using similar strategies as are disclosed herein for use with yeast cells. Inhibitors can be assayed on a limited scale by simply treating cells which have been transiently co-transfected with a reporter gene, a bait fusion protein gene and a prey fusion protein gene. One such embodiment may use the recombinant GAL4-dependent reporter gene construct and the GAL4-bait and TUP1-prey expression plasmids (see above). Inhibition of the RTA interaction will cause elevated reporter gene expression relative to untreated control samples. Because transient transfections can result in some variability in gene expression from sample to sample, It may be preferable for quantitation of the effect of an inhibitor to require multiple independent transient transfections (for example four or five independent samples) to obtain statistically significant results.

To reduce the number of independent samples required for accurate assessment of different inhibitors, it may be advantageous to construct a cell line, using the cell type of interest, which bears an integrated reporter gene and expression plasmids for the bait and prey fusion proteins. In order to facilitate verification of the integrity of the bait and prey fusions in the constructed cell line, it may be useful to express the prey fusion protein from an inducible promoter so that the interaction of the bait and prey may be turned off or on at will. For mammalian cells, an inducible promoter such as the MMTV-LTR may be used. The MMTV-LTR promoter is inducible by the presence of the glucocorticoid steroid dexamethasone. Thus, in such a tester cell line a reporter gene, such as a GAL4-dependent reporter gene, may be expressed in the absence of dexamethasone, but will be inhibited when the prey fusion protein gene is induced by the presence of dexamethasone. The effect of a protein-protein interaction inhibitor may accordingly be determined by measuring reporter gene expression following addition of the compound of interest to cells which have received a prior treatment with an inducing amount of dexamethasone. The use of an inducible promoter for the prey fusion protein allows the integrity of the RTA system to be assayed in a stably transfected cell line, specific for a defined RTA protein-protein interaction of interest. The stability of the cell line in conjunction with the assay for viability of the RTA system may facilitate use of such a cell line for automated screening of specific inhibitors.

EXAMPLES

In the following examples, techniques for genetic and biochemical manipulations of yeasts are as described previously (18). Standard protocols for recombinant DNA are employed for construction of the bait and prey expression plasmids and the reporter genes (2).

Characterization of GAL4-GAL80 interaction in vivo using TUP1-GAL80 fusions

Induction of the GAL genes involves a galactose-induced change in the interaction between the transcriptional activator GAL4 and its negative regulatory protein GAL80. To examine interaction between GAL4 and GAL80 under inducing and non-inducing (37) conditions in vivo using the RTA assay of the invention, yeast expression plasmids were constructed which produced a prey fusion protein having the TUP1 repression domain and a heterologous GAL80 amino acid sequence. TUP1 was fused to the C-terminus of GAL80. The recombinant gene coding for the prey fusion protein was expressed from the ADH1 promoter on 2 micron plasmid vectors. GAL80, TUP1, and GAL80-TUP1 fusion proteins were co-expressed with GAL4 protein in a yeast strain which contained a GAL1-HIS3 reporter gene. Activation of the reporter gene was determined by the ability of the yeast to grow in the absence of histidine (Table 3). GAL4 was capable of inducing the expression of the GAL1-HIS3 reporter gene, as determined by growth on galactose plates lacking histidine, when co-expressed with GAL80 or the N-terminus of TUP1. The chimeric protein consisting of GAL80 fused at its C-terminus to N-terminal TUP1 repression domain (GAL80-TUP1(1–200)) had no effect on the ability of GAL4 to activate the GAL1-HIS3 reporter gene (Table 3).

TABLE 3

The TUP1 repression domain inhibits transactivation by GAL4 when fused to the N-terminus of GAL80.

| Bait Protein | Prey Protein | Growth on SG-His[a] |
|---|---|---|
| GAL4 | None | ++++ |
| GAL4 | GAL80 | +++ |
| GAL4 | TUP1 (1-200) | ++++ |
| GAL4 | GAL80-TUP1 (1-200) | ++++ |
| GAL4 | TUP1 (1-200) -GAL80 | − |

[a]Yeast were transformed with the bait and prey expression plasmids and streaked onto synthetic galactose (SG) plates lacking histidine. Growth was scored after three days: ++++, full growth; −, no growth.

The N-terminal 200 amino acid long repressor domain of TUP1 was fused to the N-terminus of GAL80 to create a prey fusion protein designated TUP1(1–200)-GAL80. In contrast to the result observed with the GAL80-TUP1 fusion protein, the TUP1(1–200)-GAL80 prey fusion protein repressed the ability of GAL4 to activate transcription of the GAL1-HIS3 reporter gene on galactose, as determined by the inability of yeast expressing this protein to grow in the absence of histidine (Table 3). This result demonstrates that the TUP1 repression domain can inhibit the ability of GAL4 to activate transcription when fused to the N-terminus, but not the C-terminus, of GAL80.

To examine the effect of the TUP1-GAL80 fusion protein on GAL4 activity in cells growing in inducing and non-inducing conditions, the experiments described above were repeated using a GAL1-URA3 reporter gene which could be counter-selected and in which GAL4 protein was over expressed. Activation of the GAL1-URA3 reporter gene can be assayed by growth on medium lacking uracil, while repression of URA3 expression can be detected by growth in the presence of the pyrimidine analog 5-fluoroorotic acid (see Table 1). TUP1-GAL80 strongly inhibited transcriptional activation by over expressed GAL4 in medium containing glucose, galactose, or raffinose, while neither GAL80 nor TUP1 alone were able to prevent GAL4 activity under these conditions (Table 4). These results indicates that the N-terminal repression domain of TUP1, when fused to GAL80 can prevent transcriptional activation by GAL4, even when GAL4 is expressed at high levels, under both inducing and non-inducing conditions.

TABLE 4

TUP1-GAL80 prevents transcriptional activation of a GAL1-URA3 reporter gene by GAL4 in both inducing and non-inducing conditions.

| Bait Protein[a] | Prey Protein | Carbon Source | Growth on 5-FOA[b] |
|---|---|---|---|
| GAL4 (1-881) | None | galactose | − |
| GAL4 (1-881) | None | glucose | − |
| GAL4 (1-881) | None | raffinose | − |
| GAL4 (1-881) | GAL80 | galactose | − |
| GAL4 (1-881) | GAL80 | glucose | − |
| GAL4 (1-881) | GAL80 | raffinose | − |
| GAL4 (1-881) | TUP1 | galactose | − |
| GAL4 (1-881) | TUP1 | glucose | − |
| GAL4 (1-881) | TUP1 | raffinose | − |
| GAL4 (1-881) | TUP1-GAL80 | galactose | ++++ |
| GAL4 (1-881) | TUP1-GAL80 | glucose | ++++ |
| GAL4 (1-881) | TUP1-GAL80 | raffinose | ++++ |

[a]GAL4 protein was over expressed from the ADH1 promoter on a 2 micron plasmid.
[b]Yeast were transformed with the bait and prey expression plasmids and streaked onto synthetic medium containing the indicated carbon source in the presence of 0.1% 5-FOA. Growth was scored after three days: ++++, full growth; −, no growth.

To examine whether specific interaction between GAL4 and GAL80 was required for the effect of TUP1-GAL80 on GAL4's activity, the RTA assay of the invention was used to test the effect of TUP1-GAL80 on a GAL4 derivative from which the C-terminal 30 amino acids of GAL4 were deleted. A GAL4 derivative consisting of residues 1–848, which lacks the C-terminal GAL80-interaction segment (see FIG. 2), was not inhibited by TUP1-GAL80. A strain containing the GAL1-URA3 reporter gene expressing GAL4(1–848) and TUP1-GAL80 was incapable of growing on 5-FOA (Table 5). This result indicates that the TUP1-GAL80 protein only inhibits transcriptional activation by a GAL4 derivative with which it can form a specific interaction.

TABLE 5

The C-terminal 30 amino acids of GAL4 are necessary for the repressive effect of TUP1-GAL80 of a GAL1-URA3 reporter gene.

| Bait Protein[a] | Prey Protein | Carbon Source | Growth on 5-FOA[b] |
| --- | --- | --- | --- |
| GAL4 (1-881) | None | galactose | – |
| GAL4 (1-881) | GAL80 | galactose | – |
| GAL4 (1-881) | TUP1 | galactose | – |
| GAL4 (1-881) | TUP1-GAL80 | galactose | ++++ |
| GAL4 (1-848) | None | galactose | – |
| GAL4 (1-848) | GAL80 | galactose | – |
| GAL4 (1-848) | TUP1 | galactose | – |
| GAL4 (1-848) | TUP1-GAL80 | galactose | – |

[a]GAL4 proteins were over expressed from the ADH1 promoter on a 2 micron plasmid.
[b]Yeast were transformed with the bait and prey expression plasmids and streaked onto synthetic medium containing the indicated carbon source in the presence of 0.1% 5-FOA. Growth was scored after three days: ++++, full growth; –, no growth.

Figure 11:
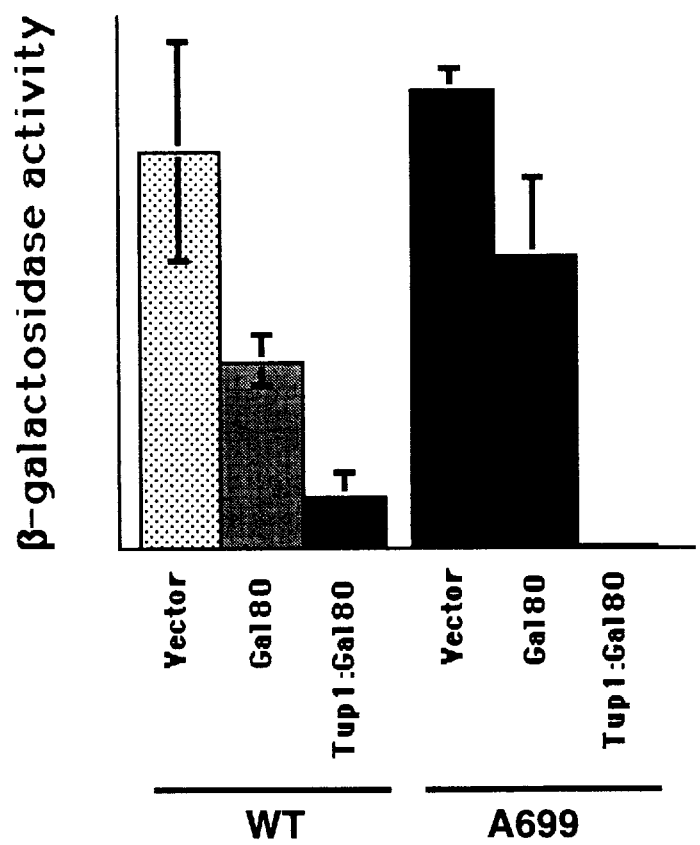
FIG. 11: Bar graph showing that the RTA system can detect the effect of serine 699 phosphorylation on GAL4-GAL80 interaction in vivo. Yeast containing a GAL1-LacZ reporter gene, and over expressing wild type GAL4 (WT) or the GAL4 S699A mutation (A699), were transformed with plasmids expressing GAL80 (GAL80), TUP1-GAL80 (TUP1/Gal80), or a vector control (vector). Cells were grown to mid-log phase and then assayed for LacZ transcription by determination of beta-galactosidase activity.

Phosphorylation at GAL4 serine 699 regulates the affinity of GAL4-GAL80 interaction in vivo as measured by the RTA system The RTA assay of the invention was used to examine the effect of phosphorylation at serine 699 of GAL4 on GAL4-GAL80 interaction. The effect of the TUP1-GAL80 fusion on transcriptional activation by wild type GAL4 and GAL4 bearing the S699A mutation were compared in a yeast strain bearing a GAL1-LacZ reporter gene. When over expressed, both GAL4 and GAL4 S699A cause efficient activation of this reporter gene in the presence of either GAL80 or TUP1 alone, as measured by beta-galactosidase activity (FIG. 11). However, the TUP1-GAL80 fusion inhibited transcriptional activation by GAL4 S699A significantly more than it inhibited wild type GAL4 (FIG. 11), indicating that the phosphorylation at serine 699 weakens the interaction between GAL4 and GAL80.

Interaction between GAL4 and SUG1 may be detected in vivo by RTA assay

The RTA assay of the invention was used to examined the interaction between GAL4 and the 26S proteosome subunit encoded by SUG1 using a GAL1-HIS3 reporter gene. Neither SUG1 nor the TUP1 repression domain expressed independently had an effect on the ability of GAL4 to activate GAL1-HIS3 transcription, which was indicated by the ability to grow in the absence of histidine. The TUP1-SUG1 fusion caused significantly slower growth on SD-His, indicating that this fusion inhibited GAL4's ability to activate the GAL1-HIS3 reporter gene.

TABLE 6

Interaction between GAL4 and SUG1 detected by RTA using a GAL1-HIS3 reporter gene.

| Bait Protein | Prey Protein | Growth on SG-His[a] |
| --- | --- | --- |
| GAL4 | None | ++++ |
| GAL4 | SUG1 | ++++ |
| GAL4 | TUP1 (1-200) | ++++ |
| GAL4 | TUP1 (1-200) -SUG1 | + |

[a]Yeast were transformed with the bait and prey expression plasmids and streaked onto synthetic galactose (SG) plates lacking histidine. Growth was scored after three days: ++++, full growth; –, no growth.

Sensitivity of the GAL1-URA3 reporter gene can be adjusted by the 5-FOA concentration The concentration of 5-FOA may be adjusted to enable detection of weaker protein-protein interactions using the RTA assay of the invention. Using lower concentrations of 5-FOA selects for weaker repression by the prey fusion and facilitates detection of the differential repressive effect of the TUP1-GAL80 and GAL80 proteins on over expressed GAL4. The TUP1-GAL80 prey fusion protein allowed growth of yeast bearing the GAL1-URA3 reporter gene, and over expressing wild type GAL4 protein, on concentrations of 5-FOA up to 0.1% (Table 7). In contrast, GAL80 protein alone allowed only minimal growth on medium containing 0.05% 5-FOA, but significant growth on 0.01% 5-FOA. This result indicates that the TUP1-GAL80 protein may be 5–10 fold more efficient at inhibiting transcriptional activation by over expressed GAL4 than is GAL80 protein alone. This indicates that by varying the concentration of 5-FOA in the selective medium, the RTA assay of the invention may be adjusted to select for weak or strong interactions between bait and prey fusions.

TABLE 7

Effect of the 5-FOA concentration on the sensitivity of the GAL1-URA3 reporter gene.

| Bait | Prey | 5-FOA Concentration (% W/V)[a] | | | | |
| --- | --- | --- | --- | --- | --- | --- |
| | | 0 | 0.01 | 0.05 | 0.1 | 0.2 |
| GAL4 | None | ++++ | – | – | – | – |
| GAL4 | TUP1-GAL80 | ++++ | ++++ | ++++ | +++ | – |
| GAL4 | GAL80 | ++++ | ++++ | ++ | – | – |

[a]Yeast cells expressing the bait and prey proteins were patched onto glucose-containing minimal medium containing 5-FOA at the indicated concentration. Growth of the yeast was scored after three days: ++++, full growth; –, no growth.

The RTA assay can be used to identify a specific protein-protein interaction from a library In this aspect of the RTA assay, selection with 5-FOA for repression of the GAL1-URA3 reporter gene may be used to screen libraries for specific protein-protein interactions. Plasmids expressing TUP1, GAL80 and TUP1-GAL80 were added to an existing yeast plasmid library. To 10 micrograms of plasmid library we added 10 micrograms each of the TUP1 and GAL80 expression plasmids, and 1 nanogram of the TUP1-GAL80 expression plasmid. The plasmid mixture was then transformed into yeast containing a plasmid expressing wild type GAL4, and which contained the GAL1-URA3 reporter gene. Library transformants were spread on plates containing 0.1% 5-FOA and allowed to grow for three days. From a transformation of 10 micrograms total, 24 colonies were picked which grew rapidly on 5-FOA, indicating repression of the URA3 reporter gene. Plasmid DNA was recovered from the 5-FOA resistant colonies by transformation into E. coli, and analysed by restriction endonuclease digestion. DNA recovered from each of the 5-FOA resistant colonies represented the original GAL4 expression plasmid or the TUP1-GAL80 expression plasmid. One colony contained a rearranged form of the GAL4 expression plasmid. Plasmids were not recovered which expressed GAL80 or TUP1 alone, or plasmids from the original yeast library. This experiment indicates that counterselectable reporter genes may be used in accordance with the RTA assay of the invention to identify protein-protein interactions from plasmid libraries. Also, the fact that one of the 24 colonies contained a rearranged GAL4 expression plasmid underscores the advantages associated with expression the prey fusion proteins from a regulatable promoter in order to facilitate verification of the integrity of the bait following the initial screen.

Figure 12:
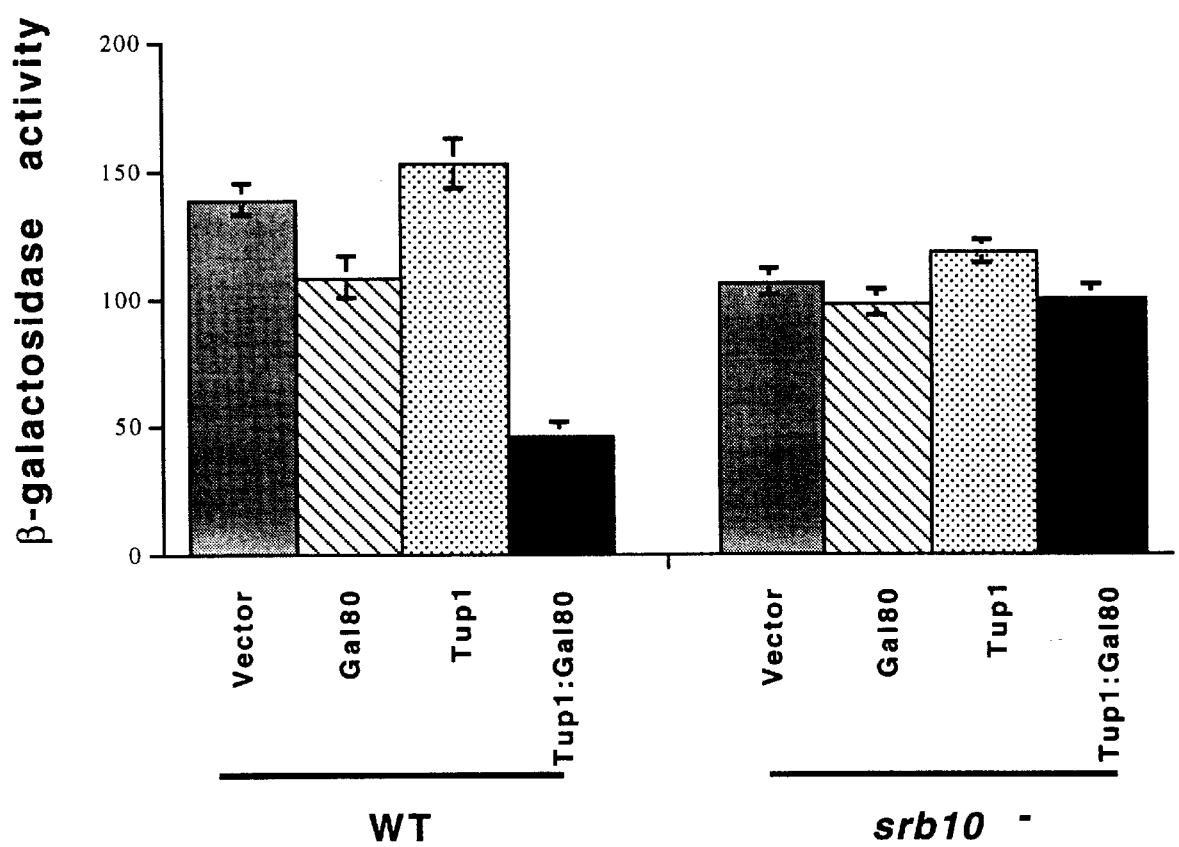
FIG. 12: Bar graph showing that the inhibitory effect of the TUP1 repression domain in one embodiment of the RTA interaction requires SRB10. Wild type yeast (WT), or srb10⁻ yeast (srb10⁻) over expressing wild type GAL4 containing a GAL1-LacZ reporter gene were transformed with plasmids expressing GAL80 (GAL80), TUP1 (TUP1), TUP1-GAL80 (TUP1:Gal80), or a vector control (vector). Cells were grown to mid-log phase and then assayed for LacZ transcription by determination of beta-galactosidase activity.

The N-terminal TUP1 repression domain requires SRB10 for its function in the RTA system Genetic analysis of TUP1 function suggests that it requires components of the RNA polymerase holoenzyme for its function. In particular, the holoenzyme-associated cyclin-dependent protein kinase SRB10 is required for repression of transcription by TUP1 (48). To determine whether the TUP1 repression domain functions normally in an RTA interaction, the ability of the TUP1-GAL80 fusion to inhibit transcription in an srb10⁻ strain was assayed. Over expressed GAL4 activated transcription of a GAL1-LacZ reporter gene normally in this strain (FIG. 12). Neither GAL80 nor TUP1 expressed alone in combination with GAL4 had a significant effect on LacZ transcription. In contrast to the result observed in wild type yeast, the TUP1-GAL80 fusion had no effect on transcriptional activation by GAL4 in the srb10⁻ strain (FIG. 12). This result indicates that interaction between the GAL4-bait and TUP1-prey fusions in an RTA interaction has characteristics similar to the normal functioning of the TUP1 protein.

References

The following documents are incorporated herein by reference:

1. Anderson, M. T., I. M. Tjioe, M. C. Lorincz, D. R. Parks, L. A. Herzenberg, G. P. Nolan, and L. A. Herzenberg. 1996. Simultaneous fluorescence-activated cell sorter analysis of two distinct transcriptional elements within a single cell using engineered green fluorescent proteins. Proc Natl Acad Sci U.S.A. 93:8508–11.
2. Ausubel, F. M., R. Brent, R. Kingston, D. D. Moore, J. G. Seidman, J. A. Smith, and K. Struhl (ed.). 1994. Current Protocols in Molecular Biology. John Wiley and Sons.
3. Barberis, A., J. Pearlberg, N. Simkovich, S. Farrell, P. Reinagel, C. Bamdad, G. Sigal, and M. Ptashne. 1995. Contact with a component of the polymerase II holoenzyme suffices for gene activation. Cell 81:359–68.
4. Berger, J., J. Hauber, R. Hauber, R. Geiger, and B. R. Cullen. 1988. Secreted placental alkaline phosphatase: a powerful new quantitative indicator of gene expression in eukaryotic cells. Gene 66:1–10.
5. Boeke, J. D., F. LaCroute, and G. R. Fink. 1984. A positive selection for mutants lacking orotidine-5'-phosphate decarboxylase activity in yeast: 5-fluoro-orotic acid resistance. Mol Gen Genet 197:345–6.
6. Brent, R., J. Gyuris, and E. Golemis. 1996. U.S. Pat. No. 5,580,736.
7. Brent, R., and M. Ptashne. 1985. A eukaryotic transcriptional activator bearing the DNA specificity of a prokaryotic repressor. Cell 43:729–36.
8. Brunelli, J. P., and M. L. Pall. 1993. A series of yeast/Escherichia coli lambda expression vectors designed for directional cloning of cDNAs and cre/lox-mediated plasmid excision. Yeast 9:1309–18.
9. Chatoo, B. B., F. Sherman, D. A. Azubalis, D. Fjellstedt, D. Mehnert, and M. Ogur. 1978. LYS2. Genetics 93:51–55.
10. Chien, C. T., P. L. Bartel, R. Sternglanz, and S. Fields. 1991. The two-hybrid system: a method to identify and clone genes for proteins that interact with a protein of interest. Proc Natl Acad Sci U.S.A. 88:9578–82.
11. Cocker, J. H., S. Piatti, C. Santocanale, K. Nasmyth, and J. F. X. Diffley. 1996. An essential role for the Cdc6 protein in forming the pre-replicative complexes of budding yeast. Nature 379:180–182.
12. Edmondson, D. G., M. M. Smith, and S. Y. Roth. 1996. Repression domain of the yeast global repressor Tup1 interacts directly with histones H3 and H4. Genes Dev 10:1247–59.
13. Fearon, E. R., T. Finkel, M. L. Gillison, S. P. Kennedy, J. F. Casella, G. F. Tomaselli, J. S. Morrow, and C. Van Dang. 1992. Karyoplasmic interaction selection strategy: a general strategy to detect protein-protein interactions in mammalian cells. Proc Natl Acad Sci U.S.A. 89:7958–62.
14. Fields, S., and O. Song. 1989. A novel genetic system to detect protein-protein interactions. Nature 340:245–6.
15. Fields, S., and O.-K. Song. 1994. U.S. Pat. No. 5,283,173.
16. Fields, S., and O.-K. Song. 1995. U.S. Pat. No. 5,468,614.
17. Goffeau, A., B. G. Barrell, H. Bussey, R. W. Davis, B. Dujon, H. Feldmann, F. Galibert, J. D. Hoheisel, C. Jacq, M. Johnston, E. J. Louis, H. W. Mewes, Y. Murakami, P. Philippsen, H. Tettelin, and S. G. Oliver. 1996. Life with 6000 genes. Science 274:546, 563–7.
18. Guthrie, C., and G. R. Fink (ed.). 1991. Guide to Yeast Genetics and Molecular Biology, vol. 194.
19. Hanna-Rose, W., and U. Hansen. 1996. Active repression mechanisms of eukaryotic transcription repressors. Trends Genet 12:229–34.
21. Hoffmann, W. 1995. Molecular characterization of the CAN1 locus in Saccharomyces cerevisiae. A transmembrane protein without N-terminal hydrophobic signal sequence. J. Biol. Chem. 260:11831–7.
20. Herzing, L. B., and M. S. Meyn. 1993. Novel lacZ-based recombination vectors for mammalian cells. Gene 137:163–9.
22. Johnston, M., and J. Dover. 1988. Mutational Analysis of the GAL4-Encoded Transcriptional Activator Protein of Saccharomyces cerevisiae. Genetics 120:63–74.
23. Kanazawa, S., M. Driscoll, and K. Struhl. 1988. ATR1, a Saccharomyces cerevisiae gene encoding a transmembrane protein required for aminotriazole resistance. Mol Cell Biol 8:664–73.
24. Kaufer, N. F., H. M. Fried, W. F. Schwindinger, M. Jasin, and J. R. Warner. 1983. Cycloheximide resistance in yeast: the gene and its protein. Nucleic Acids Res 11:3123–35.
25. Keleher, C. A., M. J. Redd, J. Schultz, M. Carlson, and A. D. Johnson. 1992. Ssn6-Tup1 is a general repressor of transcription in yeast. Cell 68:709–19.
26. Korneev, S., S. Blackshaw, and J. A. Davies. 1994. cDNA libraries from a few neural cells. Prog Neurobiol 42:339–46.
27. Leanna, C. A., and M. Hannink. 1996. The reverse two-hybrid system: a genetic scheme for selection against specific protein/protein interactions. Nucleic Acids Res 24:3341–7.
28. Leuther, K., and S. A. Johnston. 1992. Nondissociation of GAL4 and GAL80 in Vivo After Galactose Induction. Science 256:1333–1335.
29. Ma, J., and M. Ptashne. 1987. The carboxy-terminal 30 amino acids of GAL4 are recognized by GAL80. Cell 50:137–42.
30. Ma, J., and M. Ptashne. 1988. Converting a eukaryotic transcriptional inhibitor into an activator. Cell 55:443–6.
31. Ma, J., and M. Ptashne. 1987. A new class of yeast transcriptional activators. Cell 51:113–9.
32. Pawson, T. 1995. Protein modules and signalling networks. Nature 373:573–80.
33. Ptashne, M. 1988. How Eukaryotic Transcriptional Activators Work. Nature 335:683–689.
34. Ruden, D. M., J. Ma, Y. Li, K. Wood, and M. Ptashne. 1991. Generating yeast transcriptional activators containing no yeast protein sequences. Nature 350:250–2.
35. Sadowski, I. 1995. Uses for GAL4 expression in mammalian cells. Genet Eng (N Y) 1995;17:119–48

36. Sadowski, I., B. Bell, P. Broad, and M. Hollis. 1992. GAL4 fusion vectors for expression in yeast or mammalian cells. Gene 118:137–41.
37. Sadowski, I., C. Costa, and R. Dhanawansa. 1996. Phosphorylation of Gal4p at a single C-terminal residue is necessary for galactose-inducible transcription. Mol Cell Biol 16:4879–87.
38. Sadowski, I., J. Ma, S. Triezenberg, and M. Ptashne. 1988. GAL4-VP16 is an unusually potent transcriptional activator. Nature 335:563–4.
39. Sadowski, I., D. Niedbala, K. Wood, and M. Ptashne. 1991. GAL4 is phosphorylated as a consequence of transcriptional activation. Proc Natl Acad Sci U.S.A. 88:10510–4.
40. Scherer, S., and R. W. Davis. 1979. Replacement of chromosome segments with altered DNA sequences constructed in vitro. Proc Natl Acad Sci U.S.A. 76:4951–5.
41. Singh, A., and F. Sherman. 1975. Genetic and physiological characterization of met15 mutants of *Saccharomyces cerevisiae*: a selective system for forward and reverse mutations. Genetics 81:75–97.
42. Stargell, L. A., and K. Struhl. 1996. Mechanisms of transcriptional activation in vivo: two steps forward. Trends Genet 12:311–5.
43. Stern, S., and W. Herr. 1991. The herpes simplex virus trans-activator VP16 recognizes the Oct-1 homeo domain: evidence for a homeo domain recognition subdomain. Genes Dev 5:2555–66.
44. Swaffield, J. C., K. Melcher, and S. A. Johnston. 1995. A highly conserved ATPase protein as a mediator between acidic activation domains and the TATA-binding protein. Nature 374:88–91.
45. Treitel, M. A., and M. Carlson. 1995. Repression by SSN6-TUP1 is directed by MIG1, a repressor/activator protein. Proc Natl Acad Sci U.S.A. 92:3132–6.
46. Triezenberg, S. J., R. C. Kingsbury, and S. L. McKnight. 1988. Functional dissection of VP16, the trans-activator of herpes simplex virus immediate early gene expression. Genes Dev 2:718–29.
47. Tzamarias, D., and K. Struhl. 1994. Functional dissection of the yeast Cyc8-Tup1 transcriptional co-repressor complex. Nature 369:758–61.
48. Vallier, L. G., and M. Carlson. 1994. Synergistic release from glucose repression by mig1 and ssn mutations in *Saccharomyces cerevisiae*. Genetics 137:49–54.
49. Vasavada, H. A., S. Ganguly, F. J. Germino, Z. X. Wang, and S. M. Weissman. 1991. A contingent replication assay for the detection of protein-protein interactions in animal cells. Proc. Natl. Acad. Sci. U.S.A. 88:10686–10690.
50. Wahi, M., and A. D. Johnson. 1995. Identification of genes required for alpha 2 repression in Saccharomyces cerevisiae. Genetics 140:79–90.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

We claim:

1. Cells for assaying interactions between fusion proteins, the cells comprising:
a first recombinant gene coding for a prey fusion protein, the prey fusion protein comprising a transcriptional repressor domain and a first heterologous amino acid sequence;
a second recombinant gene coding for a bait fusion protein, the bait fusion protein comprising a DNA-binding domain and a second heterologous amino acid sequence; and,
a recombinant reporter gene coding for a detectable gene product, the recombinant reporter gene comprising an operator DNA sequence capable of binding to the DNA binding domain of the bait fusion protein;
wherein the reporter gene is expressed in the absence of binding between the first heterologous amino acid sequence and the second heterologous amino acid sequence and the reporter gene is repressed when there is binding between the first heterologous amino acid sequence and the second heterologous amino acid sequence.

2. The cells of claim 1 wherein the bait fusion protein further comprises a transcriptional activator domain.

3. The cells of claim 2, wherein the bait fusion protein comprises amino acids 1–238 of GAL4.

4. The cells of claim 1 wherein the first recombinant gene is under the control of a repressable promoter.

5. The cells of claim 4, wherein the repressible promoter is the MET3 promoter.

6. The cells of claim 1, wherein the DNA-binding domain comprises a DNA-binding domain of GAL4.

7. The cells of claim 1, wherein the DNA-binding domain comprises a DNA-binding domain of LexA.

8. The cells of claim 1 wherein the transcriptional repressor domain comprises an amino acid sequence selected from the group consisting of a transcriptional repressor domain of the yeast TUP1 protein, a transcriptional repressor domain of the *Drosophila Kruppel* protein, a transcriptional repressor domain of the Drosophila engrailed protein, a transcriptional repressor domain of the *Drosophila knirps* protein, a transcriptional repressor domain of the Drosophila even-skipped protein, a transcriptional repressor domain of the Drosophila paired protein, a transcriptional repressor domain of the mammalian Egr-1 protein, a transcriptional repressor domain of the mammalian WT1 protein, a transcriptional repressor domain of the mammalian RARa protein, and a transcriptional repressor domain of the mammalian KRAB protein.

9. The cells of claim 1 wherein the cells are selected from the group consisting of *Saccharomyces cerevisiae* cells, *Schizosacharomyces pombe* cells, and mammalian tissue culture cells.

10. The cells of claim 1 wherein the cells are yeast cells and the reporter gene is selected from the group consisting of the yeast URA3 gene, the yeast CAN1 gene, the yeast GAL1 gene, the yeast HIS3 gene, and the *E. coli* LacZ gene.

11. The cells of claim 1 wherein the cells are mammalian cells and the reporter gene is selected from the group consisting of the CAT gene, the LacZ gene, the SEAP gene, the Luciferase gene, the GFP gene, the BFP gene, the CD2 gene, the Flu HA gene, and the tPA gene.

12. The cells of claim 1 wherein the operator of the reporter gene further comprises a binding site for a trans-activator protein.

13. The cells of claim 12, wherein the transactivator protein is GCN4.

14. A kit for making cells for assaying interactions between fusion proteins, the kit comprising:
a first vector for expressing a prey fusion protein having a transcriptional repressor domain, the first vector comprising an expressable gene having a first insertion site and having a sequence coding for the transcriptional repressor domain;
a second vector for expressing a bait fusion protein having a DNA-binding domain, the second vector comprising an expressable gene having a second insertion site and having a sequence coding for the DNA-binding domain; and, host cells having a recombinant reporter gene coding for a detectable gene product, the recombinant reporter gene comprising an operator DNA sequence capable of binding to the DNA binding domain of the bait fusion protein, wherein the reporter gene is expressed in the absence of binding between the prey fusion protein and the bait fusion protein and the reporter gene is repressed when there is binding between the prey fusion protein and the bait fusion protein.

15. The kit of claim 14, wherein the cells are yeast cells; the transcriptional repressor domain comprises an amino acid sequence homologous to a transcriptional repressor domain of a TUP1 protein;

the DNA-binding domain comprises an amino acid sequence homologous to a DNA-binding sequence of a GAL4 protein;

the operator of the reporter gene comprises a DNA sequence homologous to a GAL4 protein binding sequence of a GAL1gene;

the reporter gene comprises a coding sequence homologous to a coding sequence selected from the group consisting of the coding sequences of the CAN1 gene, the URA3 gene and the LacZ gene.

16. The kit of claim 15, wherein the second vector is selected from the group consisting of the pY and pG plasmids.

17. The kit of claim 15, further comprising oligonucleotide primers homologous to sequences flanking the first and second insertion sites.

18. The kit of claim 15, wherein the first vector is selected from the group consisting of the pBDH and PBDL plasmids.

19. A method of assaying for interactions between fusion proteins in cells, the method comprising:

causing the cells to express a recombinant gene coding for a prey fusion protein, the prey fusion protein comprising a transcriptional repressor domain and a first heterologous amino acid sequence;

causing the cells to express a recombinant gene coding for a bait fusion protein, the bait fusion protein comprising a DNA-binding domain and a second heterologous amino acid sequence;

providing the cells with a recombinant reporter gene coding for a detectable gene product, the recombinant reporter gene comprising an operator DNA sequence capable of binding to the DNA-binding domain of the bait fusion protein, wherein the reporter gene is expressed in the absence of binding between the first heterologous amino acid sequence and the second heterologous amino acid sequence and the reporter gene is repressed when there is binding between the first heterologous amino acid sequence and the second heterologous amino acid sequence; and assaying for expression of the detectable gene product.

20. The method of claim 19, wherein the cells are yeast cells, the reporter gene comprises a coding sequence homologous to the coding sequence of the CAN1 gene, and the step of assaying for expression of the detectable gene product comprises growing the cells on canavanine.

21. The method of claim 19, wherein the cells are yeast cells, the reporter gene comprises a coding sequence homologous to the coding sequence of the URA3 gene, and the step of assaying for expression of the detectable gene product comprises growing the cells on 5-FOA.

22. The method of claim 19, wherein the cells are yeast cells, the reporter gene comprises a coding sequence homologous to the coding sequence of the GAL1gene, and the step of assaying for expression of the detectable gene product comprises growing the cells on 2-deoxygalactose.

23. The method of claim 19, wherein the cells are yeast cells, the reporter gene comprises a coding sequence homologous to the coding sequence of the LacZ gene, and the step of assaying for expression of the detectable gene product comprises growing the cells on X-gal.

24. The method of claim 19, wherein the cells are yeast cells, the reporter gene comprises a coding sequence homologous to the coding sequence of the HIS3 gene, and the step of assaying for expression of the detectable gene product comprises growing the cells on medium lacking histidine.

25. A method of assaying the ability of compounds to interfere with the interaction between fusion proteins in cells, the method comprising:

causing the cells to express a recombinant gene coding for a prey fusion protein, the prey fusion protein comprising a transcriptional repressor domain and a first heterologous amino acid sequence;

causing the cells to express a recombinant gene coding for a bait fusion protein, the bait fusion protein comprising a DNA-binding domain and a second heterologous amino acid sequence, the second heterologous amino acid sequence being capable of binding to the first heterologous amino acid sequence;

providing the cells with a recombinant reporter gene coding for a detectable gene product, the recombinant gene comprising an operator DNA sequence capable of binding to the DNA-binding domain of the bait fusion protein, wherein the reporter gene is expressed in the absence of binding between the first heterologous amino acid sequence and the second heterologous amino acid sequence and the reporter gene is repressed when there is binding between the first heterologous amino acid sequence and the second heterologous amino acid sequence;

providing the cells with an exogenous compound; and assaying for expression of the detectable gene product.

26. The method of claim 25, wherein the cells are yeast cells, the reporter gene comprises a coding sequence homologous to the coding sequence of the URA3 gene, and the step of assaying for expression of the detectable gene product comprises growing the cells on medium lacking uracil.

27. The method of claim 25, wherein the cells are yeast cells, the reporter gene comprises a coding sequence homologous to the coding sequence of the HIS3 gene, and the step of assaying for expression of the detectable gene product comprises growing the cells on medium lacking histidine.

* * * * *